US008741872B2

(12) United States Patent
Melvik et al.

(10) Patent No.: US 8,741,872 B2
(45) Date of Patent: Jun. 3, 2014

(54) SELF-GELLING ALGINATE SYSTEMS AND USES THEREOF

(71) Applicant: FMC Biopolymer AS, Sandvika (NO)

(72) Inventors: Jan Egil Melvik, Oslo (NO); Michael Dornish, Bekkestua (NO); Edvar Onsoyen, Sande (NO); Astrid B. Berge, Asker (NO); Terje Svendsen, Asker (NO)

(73) Assignee: FMC Biopolymer AS, Sandvika (NO)

( * ) Notice: Subject to any disclaimer, the term of this patent is extended or adjusted under 35 U.S.C. 154(b) by 0 days.

(21) Appl. No.: 13/930,426

(22) Filed: Jun. 28, 2013

(65) Prior Publication Data

US 2013/0288998 A1    Oct. 31, 2013

Related U.S. Application Data

(62) Division of application No. 12/855,964, filed on Aug. 13, 2010, now Pat. No. 8,481,695, which is a division of application No. 11/248,984, filed on Oct. 12, 2005, now Pat. No. 7,790,699.

(60) Provisional application No. 60/617,852, filed on Oct. 12, 2004.

(51) Int. Cl.
*A61K 31/70* (2006.01)
*C08L 5/04* (2006.01)
*C08J 3/075* (2006.01)

(52) U.S. Cl.
USPC .................................. 514/54; 514/53; 536/3

(58) Field of Classification Search
CPC ....................................................... A61K 31/70
USPC ........................................... 514/54, 53; 536/3
See application file for complete search history.

(56) References Cited

U.S. PATENT DOCUMENTS

| | | | |
|---|---|---|---|
| 1,814,981 A | 7/1931 | Thornley et al. |
| 2,420,308 A | 5/1947 | Gates et al. |
| 4,348,418 A | 9/1982 | Smith et al. |
| 4,789,734 A | 12/1988 | Pierschbacher et al. |
| 4,792,525 A | 12/1988 | Ruoslahti et al. |
| 4,879,237 A | 11/1989 | Ruoslahti et al. |
| 4,988,621 A | 1/1991 | Ruoslahti et al. |
| 5,175,093 A | 12/1992 | Seifert |
| 5,266,326 A | 11/1993 | Barry et al. |
| 5,531,716 A | 7/1996 | Luzio et al. |
| 5,874,100 A | 2/1999 | Mahoney et al. |
| 5,965,997 A | 10/1999 | Alwardi et al. |
| 6,090,763 A | 7/2000 | Stewart et al. |
| 6,121,441 A | 9/2000 | Simensen et al. |
| 6,129,761 A | 10/2000 | Hubbel |
| 6,136,334 A | 10/2000 | Viegas et al. |
| 6,146,655 A | 11/2000 | Ruben |
| 6,150,581 A | 11/2000 | Jiang et al. |
| 6,309,380 B1 | 10/2001 | Larson et al. |
| 6,407,226 B1 | 6/2002 | Simensen et al. |
| 6,432,449 B1 | 8/2002 | Goldenberg et al. |
| 6,495,161 B1 | 12/2002 | Soon-Shiong et al. |
| 6,497,902 B1 | 12/2002 | Ma |
| 6,534,083 B2 | 3/2003 | Gilding et al. |
| 6,592,566 B2 | 7/2003 | Kipke et al. |
| 6,629,947 B1 | 10/2003 | Sahatjian et al. |
| 6,638,917 B1 | 10/2003 | Li et al. |
| 6,642,363 B1 | 11/2003 | Mooney et al. |
| 6,656,508 B2 | 12/2003 | Goldenberg et al. |
| 6,730,298 B2 | 5/2004 | Griffith-Cima et al. |
| 6,793,675 B2 | 9/2004 | Shapiro et al. |
| 7,790,699 B2 | 9/2010 | Melvik et al. |
| 2001/0055588 A1 | 12/2001 | Griffith-Cima et al. |
| 2002/0001619 A1 | 1/2002 | Goldenberg et al. |
| 2003/0044391 A1 | 3/2003 | Elliott et al. |
| 2004/0037812 A1 | 2/2004 | Giannetti et al. |
| 2005/0169895 A1 | 8/2005 | Melvik et al. |
| 2006/0159823 A1 | 7/2006 | Melvik et al. |
| 2007/0054043 A1 | 3/2007 | Gaserod et al. |

FOREIGN PATENT DOCUMENTS

| | | |
|---|---|---|
| EP | A-0 345 886 | 12/1989 |
| EP | 0 849 281 A1 | 6/1998 |
| GB | 666 961 A | 2/1952 |
| GB | A-1 399 822 | 7/1975 |
| JP | 5208917 | 8/1993 |

(Continued)

OTHER PUBLICATIONS

Li Geng and Wu Jin, "Alginate and its Physical and Chemical Properties when used as a Biomacromolecule Carrier", Jiangsu Pharmacy and Clinic Research, 2002, 10(2), pp. 61-63.

Supplementary European Search Report—Jun. 16, 2008—EP 05803188.1.

Skaugrud O., et al., "Biomedical and Pharmaceutical Applications of Alginate and Chitosan", Biotechnology and Genetic Engineering Reviews, vol. 16: p. 23-40, Apr. 1999.

Andrews,R. T., et al, "Relative rates of blood reduction during transcatheter arterial embolization with tris-acryl gelatin microspheres or poly-vinyl alcohol; quantitative comparison in a swine model," *J. Vasc Intero Radio* 14,1311-1316 (2003).

(Continued)

*Primary Examiner* — Patrick Lewis
*Assistant Examiner* — Everett White
(74) *Attorney, Agent, or Firm* — FMC Corporation

(57) ABSTRACT

Kits and compositions for producing an alginate gel are disclosed. The kits and compositions comprise soluble alginate and insoluble alginate/gelling ion particles. Methods for dispensing a self-gelling alginate dispersion are disclosed. The methods comprise forming a dispersion of insoluble alginate/gelling ion particles in a solution containing soluble alginate, and dispensing the dispersion whereby the dispersion forms an alginate gel matrix. The methods may include dispensing the dispersion into the body of an individual. An alginate gel having a thickness of greater than 5 mm and a homogenous alginate matrix network and homogenous alginate gels free of one or more of: sulfates citrates, phosphates, lactates, EDTA or lipids are disclosed. Implantable devices comprising a homogenous alginate gel coating are disclosed. Methods of improving the viability of pancreatic islets, or other cellular aggregates or tissue, following isolation and during storage and transport are disclosed.

2 Claims, 11 Drawing Sheets

(56) References Cited

FOREIGN PATENT DOCUMENTS

| | | |
|---|---|---|
| JP | 09176021 A | 7/1997 |
| JP | 9-227412 A | 9/1997 |
| JP | 2000-288018 A | 10/2000 |
| WO | WO 94/10976 | 5/1994 |
| WO | WO 94/25080 | 11/1994 |
| WO | WO 97/03710 | 2/1997 |
| WO | WO 99/15211 | 4/1999 |
| WO | WO 00/09566 | 2/2000 |
| WO | WO 01/05370 | 1/2001 |
| WO | WO 03/041758 | 5/2003 |
| WO | WO 2004/011628 | 2/2004 |
| WO | WO 2004/032904 | 4/2004 |

OTHER PUBLICATIONS

Arica, B., et al, "5-Flourouracil encapsulated alginate beads for the treatment of breast cancer," *Int J Pharm* 242, 267, (2002).

Aspden, T.J., et al, "Chitosan as a nasal delivery system: evaluation of the effect of chiosan mucociliary clearance rate in the frog palate model," *Int. J Pharm* 122, 69-78, (1995).

Atala, A., et al, "Endoscopic treatment of vesicoureteral reflux with a chondrocyte-alignate suspension," *Journal of Urology* 152, 641-643(1994).

Atala, A., et al, "Injectable alginate seeded with chondrocytes as a potential treatment for vesicoureteral reflux," *Journal of Urology* 150, 745-747 (1993).

Becker, T.A., et al, "Flow properties of liquid calcium alginate polymer injected through medical microcatheters for endovascular embolization," *Journal of Biomedical Materials Research*, 61, 533-540 (2002).

Becker, T.A., et al, "Calcium alginate gel: a biocompatible and mechanically stable polymer for endovascular embolization," *Journal of Biomedical Materials Research* 54, 76-86 (2001).

Becker, T.A., et al, "In vivo assessment of calcium alginate gel for endovascular embolization of a cerebral arteriovenous malformation model using the Swine rete mirabile," *Neurosurgery* 51, 453-459 (2002).

Brunetti, P, et al, "Immunoprotection of pancreatic islet grafts within artificial microcapsules," *Int J Artific Org* 14, 789-791 (1991).

Caldamone, A.A., et al, "Long-term results of the endoscopic correction of vesicoureteral reflux in children using autologous chondrocytes," *Journal of Urology* 165, 2224-2227 (2001).

Caterson, E. J., et al, "Polymer/alginate amalgam for cartilage-tissue engineering," *Ann NY Acad Sci*, 961, 134-128 (2002).

Chang, S.C., et al, "Injection molding of chondrocyte/alignate constructs in the shape of facial implants," *Journal of Biomedical Materials Research* 55, 503-511 (2001).

Clark, A.H., et al, "Structural and mechanical properties of biopolymer gels," *Advances in Polymer Science* 83, 57-192 (1987).

Cohen, S.B., et al., "The use of absorbable co-polymer pads with alginate and cells for articular cartilage repair in rabbits," *Biomaterials* 24, 2653-2660 (2003).

de Blok, S., et al, "Fatal sepsis after uterine artery embolization with microspheres," *J Vasc Interv Radiol* 14, 779-783 (2003).

Diamond, D.A., et al, "Mechanisms of failure of endoscopic treatment of vesicoureteral reflux based on endoscopic anatomy," *Journal of Urology* 170, 1556-1559 (2003).

Diamond, D.A., et al, "Endoscopic correction of vesicoureteral refulx in children using autologous chondrocytes: preliminary results," *Journal of Urology* 162, 1185-1188 (1999).

Diduch, David R., "Marrow Stromal Cells Embedded in Alginate for repair of Osteochondral Defects," *Arthrocscopy:The Journal of Arthroscopic and Related Surgery*, (2000), vol. 16, No. 6, 571-577.

Domm, C, et al, "Redifferentiation of dedifferentiated bovine articular chondrocytes in alginate culture under low oxygen tension," *Osteoarthritis and Cartilage* 10, 13-22 (2002).

Dornish, J.M., et al, "Standards and guidelines for biopolymers in tissue-engineered medical products. ASTM alginate and chitosan standard guides," *Ann N Y Acad Sci* 944, 388-397 (2001).

Draget, K.J., "Homogeneous Alginate Gels: A Technical Approach," *Carbohydrate Polymers*, 14, 159-178, (1991).

Draget, K.I., et al, "Ionic and acid gel formation of epimerised alginates: The effect of AlgE4," *Int J Biol Macromol* 27, 117-122 (2000).

Frangonas, E. et al., "Articular cartilage repair in rabbits by using suspensions of allogenic chondrocytes in alginate," *Biomaterials* 21, 795-801 (2000).

Grant, G.T., et al, "Biological interactions between polysa ccharides and divalent cations: The egg-box model," *FEBS Lett* 32, 195, 198 (1973).

Gutowska, A., et al, "Injectable gels for tissue engineering," *Anatomical record* 263, 342-349 (2001).

Hart, A. McKay, et al, "Exogenous leukaemia inhibitory factor enhances nerve regeneration after late secondary repair using a bioartificial nerve conduit," *British Journal of Plastic Surgeons* 56, 444-450 (2003).

Hashimoto, T., et al, "Peripheral nerve regeneration through alginate gel: analysis of early outgrowth and late increase in diameter of regenerating axons," *Exp Brain Res* 146, 356-368 (2002).

Homicz, M.R., et al.,"Human septal chondrocyte redifferentiation in alginate, polyglycolic acid scaffold, and monolayer culture," *Laryngoscope* 113, 25-32 (2003).

Kataoka, K., et al, "Alginate, a bioresorbable material derived from brown seaweed, enhances elongation of amputated axons of spinal cord in infant rats," *J. Biomed Mater Res* 54, 373-384 (2001).

Kavalkovich, K.V., et al, "Chondrogenic differentiation of human mesenchymal stem cells within an alginate layer of culture system," *In Vitro Cell Dev Biol* 38, 457-466 (2002).

Kim, M.D., et al, "Uterine artery embolization for adenomyosis without fibroids," *Clin Radiol* 59, 520-526 (2004).

Knight, M.M, et al, "Cell and nucleus deformation in compressed chondrocyte-alignate constructs: temporal changes and calculation of cell modulus," *Biochim Biophys Acta* 1570, 1-8 (2002).

Kuo, C.K., et al, "Ionically crosslinked alginate hydrogels as scaffolds for tissue engineering: part 1. Structure, gelation rate and mechanical properties," *Biomaterials* 22, 511-521 (2001).

Lansdown, A.B.G., "Calcium: a potential central regulator in wound healing in the skin," *Wound Repair Regen* 10, 271:285 (2002).

Lanza, R. P., et al, "Xenotransplantation of porcine and bovine islets without immunosuppression using uncoated alginate microspheres," *Transplantation* 59, 1377-1384 (1995).

Lee, D.A., et al, "Expansion of chondrocytes for tissue engineering in alginate beads enhances chondrocytic phenotype compared to conventional monolayer techniques," *Acta Orthop Scand* 74, 6-15 (2003).

Li, S., et al, "Studies on alginate-chitosan microcapsules and renal arterial embolization in rabbits," *J Contolled Release* 84, 87-98 (2002).

Ma, P.X, "Scaffolds for tissue fabrication," *Materials Today* 7, 30-40 (2004).

Mandel, K.G., et al, "Review article: Alginate-raft formulations in the treatment of heartburn and acid reflux," *Aliment Pharmacol Ther* 14, 669-690 (2000).

Mandl, E. W., et al, "Fibroblast growth factor-2 in serum-free medium is a potent mitogen and reduces dedifferentiation of human ear chondrocytes in monolayer culture," *Matrix Biol* 23, 231-241 (2004).

Mandl, E. W., et al, "Serum-Free Medium Supplemented with High-concentration FGF2 for Cell Expansion Culture of Human Ear Chondrocytes Promotes Redifferentiation Capacity," *Tissue Eng* 8, 573-580 (2002).

Melvik, J.E., et al, "Alginate as a carrier for cell immobilization." *Fundamentals of Cell Immobilisation Biotechnology* vol. 8A. (Ed V. Nedovic and R. Willaert) Kluwer, (2004).

Melvik J.E. et al., "Key characterization parameters of alginate for use in biomedical and pharmaceutical applications," Pronova Biomedical, presented at Bioencapsulation VII, Easton, USA, (1998).

Mierisch, C.M., et al. "Chondrocyte transplantation into articular cartilage defects with use of calcium alginate: the fate of the cells," *J Bone Joint Surg Am* 85-A, 1757-1767 (2003).

(56) References Cited

OTHER PUBLICATIONS

Miralles, G., et al, "Sodium alginate sponges with or without sodium hyaluronate; In vitro engineering of cartilage," *Journal of Biomedical Materials Research* 57, 268-278 (2001).

Mosahebi, A., et al, "A novel use of alginate hydrogel as Schwann Cell matrix." *Tissue Engineering* 7, 525-534 (2001).

Orive, et al, "Cell encapsulation: promise and progress," *Nature Medicine* 9, No. 1, 104-107 (2003).

Paige, K.T., et al, "De novo cartilage generation using calcium alginate-chondrocyte constructs," *Plast Reconstr Surg* 97, 179-180 (1996).

Paige, K.T., et al, "Injectable cartilage," *Plast Reconstr Surg* 96, 1390-1398 (1995).

Risberg, B, "Adhesions: preventive strategies," *Eur J Surg Suppl* 577, 32-29 (1997).

Rowley, J.A., et al, "Alignate type and RGD density control myoblast phenotype," *Journal of Biomedical Materials Research* 60, 217-223 (2002).

Safley, S.A., et al, "Proliferative and cytokine responses in CTLA4-lg-treated diabetic NOD mice transplanted with microencapsulated neonatal porcine ICCs," *Cell Transplant* 11, 695-705 (2002).

Shapiro, L, et al, "Novel Alginate sponges for cell culture and transplantation," *Biomaterials* 18, 583-590 (1997).

Siskin, G. P., et al, "Pathologic Evaluation of a Spherical Polyvinyl Alcohol Embolic Agent in a Porcine Renal Model," *J Vasc Interv Radiol* 14, 89-98 (2003).

Skjåk-Braek, G., et al, "Application of alginate gels in biotechnology and biomedicine," *Carbohydrates in Europe* 14, 19-25 (1996).

Stevens, M. M., et, al "A rapid-curing alginate gel system: utility in periosteum-derived cartilage tissue engineering," *Biomaterials* 25, 887-894 (2004).

Storrs, R., et al, "Preclinical development of the Islet Sheet," *Ann NY Acad Sci* 944, 252-266 (2001).

Sufan, W., et al, "Sciatic nerve regeneration through alginate with tabulation or nontubulation repair in cat," *Journal of Neurotrauma* 18, 329-338 (2001).

Sutherland, I.W., "Alginates. In Biomaterials; Novel materials from biological sources," (Ed. D. Byrom) pp. 309-331, New York 1991.

Thomas S., "Alginate dressing in surgery and wound management—Part 1," *Journal of Wound Care*, vol. 9, No. 2, (2000).

Thomas S., "Alginate dressing in surgery and wound management—Part 2," *Journal of Wound Care*, vol. 9, No. 3, (2000).

Thomas S., "Alginate dressing in surgery and wound management—Part 3," *Journal of Wound Care*, vol. 9, No. 4, (2000).

Tonnesen, H.H., et al, "Alginate in drug delivery systems," *Drug Development and Industrial Pharmacy* 28, 621-630 (2002).

Tse, M., et al, "Secretion of recombinant proteins from hydroxymethyl methacrylate-methyl methacrylate capsules," *Biotechnoogy and Bioengineering* 51, 271-280 (1996).

Wang, L., et al, "Evaluation of sodium alginate for bone marrow cell tissue engineering," *Biomaterials* 24, 3475-3481(2003).

Westhaus, E., et al, "Triggered release of calcium from lipid vesicles: a bioinspired strategy for repaid gelation of polysaccharide and protein hydrogels," *Biomaterials* 22, 453-462 (2001).

Winn, S.R., et al., "Polymer-encapsulated cells genetically modified to secrete human nerve growth factor promote the survival of axotomized septal cholinergic neurons," *Proc Natl Acad Sci USA* 91, 2324-2328 (1994).

Yoon, W., "Embolic agents used for bronchial artery embolisation in massive haemoptysis," *Expert Opin Pharmacother* 5, 361-367 (2004).

SELF-GELLING ALGINATE SYSTEMS AND USES THEREOF

This application claims priority to U.S. Provisional Application Ser. No. 60/617,852 entitled Self-Gelling Alginate Systems and Uses Thereof, filed Oct. 12, 2004, which is incorporated herein by reference.

FIELD OF THE INVENTION

The present invention relates to alginate systems which have a delayed gelling process and to compositions, devices, kits and methods of making and using such systems.

BACKGROUND OF THE INVENTION

Alginates are hydrophilic marine biopolymers with the unique ability to form heat-stable gels that can develop and set at physiologically relevant temperatures. Alginates are a family of non-branched binary copolymers of 1-4 glycosidically linked β-D-mannuronic acid (M) and α-L-guluronic acid (G) residues. The relative amount of the two uronic acid monomers and their sequential arrangement along the polymer chain vary widely, depending on the origin of the alginate. Alginate is the structural polymer in marine brown algae such as *Laminaria hyperborea*, *Macrocystis pyrifera*, *Lessonia nigrescens* and *Ascophyllum nodosum*. Alginate is also produced by certain bacteria such as *Pseudomonas aeruginosa*, *Azotobacter vinelandii* and *Pseudomonas fluorescens* (WO04011628 A1).

Alginate gels are produced when a divalent cation forms ionic bonds with the negatively charged group from a G residue from each of two different alginate polymers, thereby cross-linking the two polymers. The formation of multiple cross-linkages among numerous alginate polymers results in the matrix that is the alginate gel structure.

Alginate gels can be hydrogels, i.e. cross-linked alginate polymers that contain large amounts of water without dissolution. Biopolymer gels, such as alginate hydrogels are attractive candidates for tissue engineering and other biomedical applications. Because of this and the ability to form gels under physiologic conditions, alginates are widely used and studied for encapsulation purposes and as a biostructure material. The entrapment of cells in alginate beads is a commonly used technique. Also alginates have been shown to be useful material for other types of biostructures, including tissue engineering applications and as scaffolds for nerve regenerations.

Different methods for making alginate hydrogels exist. The most common method is the dialysis/diffusion method where the alginate solution is gelled by diffusion of gelling ions from an outer reservoir. This method is mostly used when making alginate gel beads and in food applications. The manufacturing of alginate microbeads is a rapid process limited by the diffusion of gelling ions into the gel network. Although this process is well suitable for entrapment of cells in microbeads, it is less useful for the production of other shapes or structures. For manufacturing of gel structures of larger size diffusion gelling systems may have limited possibility. This is because the rapid gelling process limits the time to allow shaping of the gel structure.

A delay in the gelling process may be used to allow for the injection of solutions into the body and/or to mix cells or other biomaterial into the gel matrix prior to the gel forming. Therefore, alternative methods have been developed for the manufacturing of other types of biocompatible alginate gel structures. The gelling speed may be reduced by using internal gelling systems of which the gelling ions are released more slowly inside the forming gel. This is described as internal setting of the gel. Commonly, in an internal gelling system, a calcium salt with limited solubility, or complexed $Ca^{2+}$ ions, are mixed with an alginate solution into which the calcium ions are slowly released. Calcium sulfate has been used in alginate based cell delivery vehicles for tissue engineering. The release of calcium and gelling kinetics may also be controlled by using calcium salts with pH dependent solubility and the addition of a slowly acting acid such as D-glucono-δ-lactone (GDL). As the pH changes, calcium ions are released. Also calcium containing liposomes have been used as a controllable alginate gelling system. Alginate gel systems based upon internal gelling may have a more defined and limited supply of gelling ions as opposed to diffusion systems where calcium ions are allowed to diffuse into the alginate solution to give a calcium saturated gel.

Current methods for manufacturing of alginate gel structures have limitations. Some techniques are only useful to make gels of limited sizes and shapes. Depending of the applications there may problems associated with the control of the gelling kinetics. In some case, undesirable materials are present in gels because such materials are residues and by-products of chemically controlled gelling mechanisms. In some cases, non-physiologic pH values are required for gelling and such conditions may present limitations to the use of such methods. There is therefore a need for other gelling systems and formulations.

SUMMARY OF THE INVENTION

The present invention relates to kits for producing an alginate gel. The kits comprise a first container comprising soluble alginate, and a second container comprising insoluble alginate/gelling ion particles.

The present invention further relates to compositions for preparing alginate gels. The compositions comprise immediately soluble alginate and insoluble alginate/gelling ion particles.

The present invention further relates to methods for dispensing self-gelling alginate dispersion. The methods comprise forming a dispersion of insoluble alginate/gelling ion particles in a solution of soluble alginate, and dispensing the dispersion whereby the dispersion forms an alginate gel matrix.

The present invention further relates to methods for dispensing self-gelling alginate dispersion into an individual. The methods comprise forming a dispersion of insoluble alginate/gelling ion particles in a solution of soluble alginate, and dispensing the dispersion into an individual whereby the dispersion forms an alginate gel matrix in the individual.

The present invention further relates to methods for dispensing self-gelling alginate dispersion into an individual for use as tissue bulking material, for use in a vascular embolization procedure, for use to prevent post surgical adhesion formation, for use in wound treatment procedures, for use in diabetes treatments and for use in treatment of arthritis.

The present invention further relates to methods of using an implantable alginate gel. The methods comprise forming self gelling alginate by dispensing self gelling alginate dispersion and, following gel formation, implanting the implantable alginate gel into an individual.

The present invention further relates to methods of producing implantable devices.

The present invention further relates to alginate gels having a thickness of greater than 5 mm and a homogenous alginate matrix network.

The present invention further relates to alginate gels having a thickness of greater than 5 mm and free of one or more of: sulfates citrates, phosphates, lactates, EDTA or lipids.

The present invention further relates to implantable devices comprising a homogenous alginate gel coating.

The present invention further relates to methods filling or repairing osteochondral defects resulting from osteoarthritis by dispensing a self gelling alginate dispersion that includes chondrocytes into an individual's body or by implanting a biocompatible matrix that includes chondrocytes into an individual's body The present invention further relates to methods of treating diabetes by dispensing a self gelling alginate dispersion that includes insulin-producing cells or multicellular aggregates into an individual's body or by implanting a biocompatible matrix that includes insulin-producing cells or multicellular aggregates into an individual's body.

The present invention further relates to methods of improving the viability of pancreatic islets, or other cellular aggregates or tissue, following isolation and during storage and transport by incorporating the islets, or cellular aggregates or tissue into a self gelling alginate dispersion.

The present invention further relates to ultrapure insoluble alginate/gelling ion particles and methods of producing the same.

BRIEF DESCRIPTION OF THE FIGURES

In FIG. 5, panel A, calcium alginate (Protaweld TX 120) and sodium alginate used was each adjusted to be 1.0% of the gel. The sodium alginates used were Protanal SF 120 (69% G) and Protanal HF 60D (32% G, MW: 119 000). In FIG. 5, panel B, 5.5% strontium alginate (Example 14) was mixed with 1.25% sodium alginate at a ratio of 1:4 (final alginate concentration was 2.1%). The sodium alginates used were PRONOVA UP 100G (69% G, MW: 122 000) and PRONOVA UP 100M (46% G, MW: 119 000). The MW (and viscosity) of the two sodium alginate batches was selected to be similar (as close as possible). Each curve in FIG. 5, panel B, is the mean of three independent measurements (curves) with standard error of the mean shown for each point.

FIG. 7, panel A, shows C2C12 mouse myoblast cells 45 days after entrapment in self-gelling alginate gel. The gel was made and stored similar as in FIG. 6 but included the cells. The picture was taken using a fluorescence microscope after staining the cells with calcein (Molecular Probes, L-3224) as a marker of cell viability. Enlightened areas and spots shows the presence of viable cells. Viable cells are located inside and on the surface of the gel construct. FIG. 7, panel B, shows human chondrocytes entrapped in alginate self-gel. The gel was made of 5 ml mixed self-gel of PRONOVA SLG 20 and calcium alginate (Example 14) containing human chondrocytes. Three days after gelling the gels were sectioned into 600 μm slices using a vibratome. The gel slices was stored in cell growth medium in a $CO_2$-incubator and the picture was taken after six months. The picture was taken using a fluorescence microscope after staining the cells with calcein (Molecular Probes, L-3224) for viability and clearly shows the presence of a high number of viable cells (enlightened spots).

DETAILED DESCRIPTION OF PREFERRED EMBODIMENTS

Figure 1:
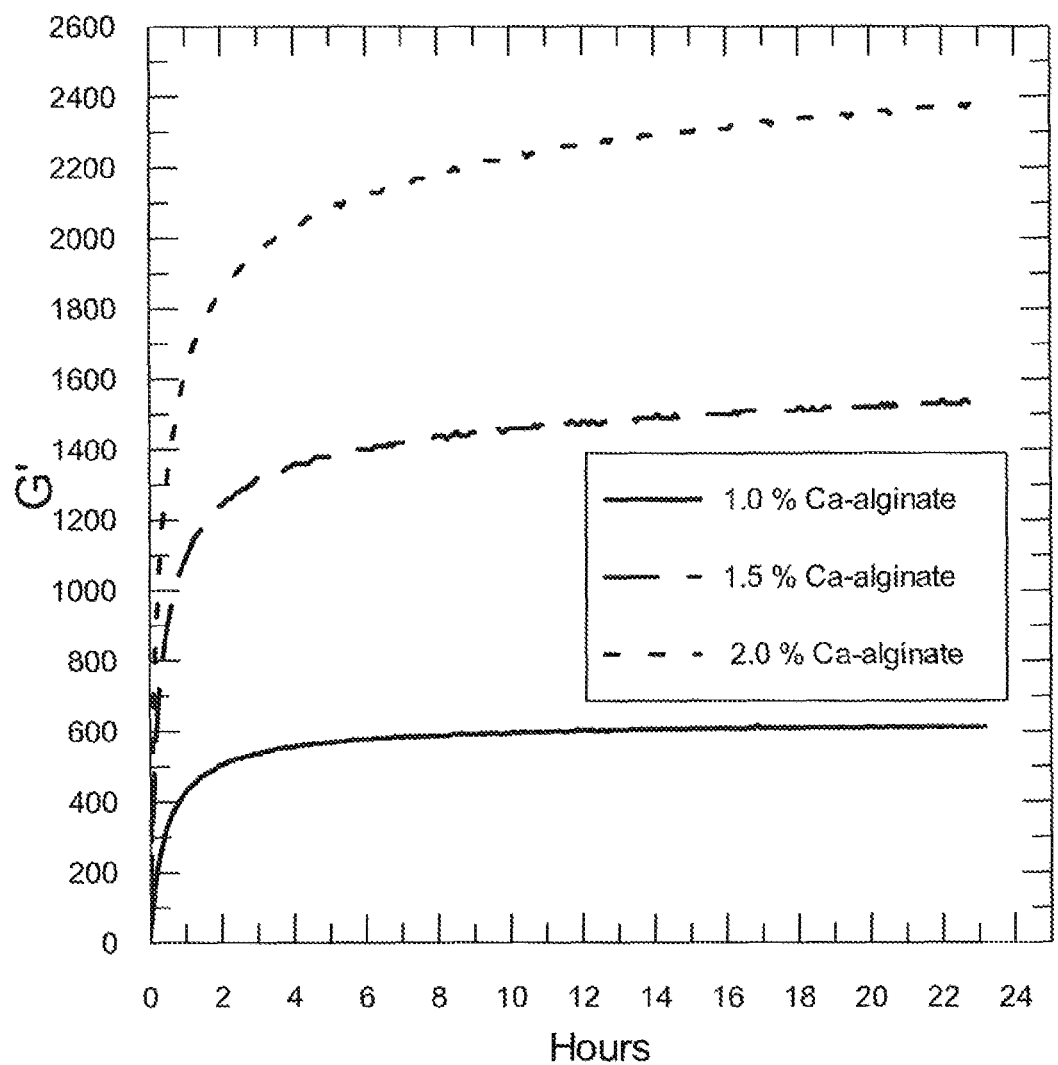
FIG. 1 contains data from rheometer measurements. Oscillation measurements were performed using a Physica MCR300 rheometer. Storage modulus as a function of time for gels with the following different calcium-alginate (Protaweld TX 120) concentrations are shown (concentrations in the mixture/gel): 1.0% calcium-alginate mixed with 1.0% sodium-alginate, and 1.5% calcium-alginate mixed with 1.0% sodium-alginate, and 2.0% calcium-alginate mixed with 1.0% sodium-alginate. The sodium alginate used was Protanal SF 120.

An alternative alginate gelling system is provided. This system is used in numerous biomedical applications as well as other applications. The system can include alginate and gelling ions that have a high degree of biocompatibility. The system provides for variations in gelling time and gel strength depending upon the needs of a specific application. The system provides gelling without the pH changes associated with other systems and requires a minimum number of components.

The system comprises two components: one is soluble alginate; the other is insoluble alginate/gelling ion particles. When the components are combined in the presence of a solvent to form a dispersion, an alginate gel begins to form as the gelling ion of the particles begins cross linking alginate polymers from the particles and the soluble alginate polymers in solution. The two components may be mixed by stirring or by using a suitable mixing device. The gelling kinetics of the formulation are dependent upon several factors including: the concentration of the soluble alginate in solution, the concentration of the insoluble alginate particles in the dispersion, the relative content of gelling ion to alginate, the presence of non-gelling ions or other carbohydrates, temperature, the size of insoluble alginate/gelling ion particles, the content of cells, multicellular aggregates, tissues or other biomaterials to be entrapped in the gel or present during gelling, (the presence of impurities) and the types of alginates used, as well as the manufacturing process for the insoluble alginate particles and post manufacturing treatment of alginate starting materials. This alginate system may therefore be widely adapted to each particular application. For entrapment of cells, multicellular aggregates, tissues or other biomaterials within the forming gel, the solvent, the alginate solution or dispersion may be premixed with the material to be entrapped.

The dispersion may be dispensed within an individual as a liquid/slurry to a site where an alginate gel matrix is desirable. Alginate gel formation, initiated when the soluble alginate and insoluble alginate/gelling ion particles are mixed in the presence of a solvent, continues and the alginate gel sets in situ. As used herein, the term "self-gelling" is meant to refer to the gelling process which occurs when the soluble alginate and insoluble alginate/gelling ion particles are mixed in the presence of a solvent. A "self gelling alginate" is an alginate dispersion or gel which includes or is formed by soluble alginate and insoluble alginate/gelling ion particles in a solvent.

The components used in the system may be maintained prior to use in any of several forms. For example, the soluble alginate may be maintained in solution or as a powder. In some embodiments, the soluble alginate may be maintained as a powder that is immediately soluble such as when it is freeze dried. Similarly, the insoluble alginate/gelling ion particles may be maintained as a dispersion or as a powder.

The alginate polymers or combinations thereof used in the soluble alginate may be the same or different from those in the insoluble alginate/gelling ion particles.

The concentration of alginate, both soluble alginate and the alginate in the form of insoluble alginate/gelling ion particles in a dispersion relative to the amount of solvent affects gelling time, porosity, stability and biodegradability, gel strength and elasticity of gels and gels having specific properties may be prepared by using specific ratios of soluble alginate and insoluble alginate/gelling ion particles to solvent. Generally, the lower the concentration of alginate (for a given ratio of soluble alginate to insoluble alginate), the more biodegradable a gel will be. In some embodiments, approximately 0.5%, 0.75%, 1%, 1.25%, 1.5%, 2%, 2.5%, 3%, 4%, 5%, 6%, 7%, 8%, 9%, 10% or more alginate (soluble alginate and alginate in the form of insoluble alginate/gelling ion particles) may be used.

The relative concentration of the soluble alginate to alginate in the form of insoluble alginate/gelling ion particles in the dispersion affects gelling time, pore size, gel strength and elasticity of gels as well as stability and biodegradability and gels having specific properties may be prepared by using specific ratios of soluble alginate to insoluble alginate/gelling ion particles. In some embodiments, the concentration of soluble alginate is approximately equal to concentration of alginate in the form of insoluble alginate/gelling ion particles (1:1). In some embodiments, the concentration of alginate in the form of insoluble alginate/gelling ion particles is twice that of soluble alginate (2:1). In some embodiments, the concentration of alginate in the form of insoluble alginate/gelling ion particles is half that of soluble alginate (1:2). In some embodiments, the concentration of alginate in the form of insoluble alginate/gelling ion particles to soluble alginate is 1 to 0.7 (1:0.7). Generally, the less gelling ion present, the more biodegradable a gel will be. Reducing the concentration of insoluble alginate/gelling ion in the system may be used to create gels with lower stability and higher biodegradability as the gel network is less saturated with cross-linking ions. Self gelling allows for the preparation of gels with lower concentrations of gelling ion to produce gels particularly well suited for biodegradable uses. In some preferred embodiments, alginate ratios of insoluble alginate/gelling ion particles to soluble alginate are: 5:1, 4:1, 3:1, 2:1, 1:1, 1:2, 1:3, 1:4 or 1:5.

The relative content of G and M monomers in the alginate polymers affects pore size, stability and biodegradability, gel strength and elasticity of gels. Alginate polymers contains large variations in the total content of M and G, and the relative content of sequence structures also varies largely (G-blocks, M-blocks and MG alternating sequences) as well as the length of the sequences along the polymer chain. Generally, the lower the G content relative to M content in the alginate polymers used the more biodegradable a gel will be. Gels with high G content alginate generally have larger pore sizes and stronger gel strength relative to gels with high M alginate, which have smaller pore sizes and lower gel strength. In some embodiments, one or more of the alginate polymers of the alginate matrix contain more than 50% $\alpha$-L-guluronic acid. In some embodiments, one or more of the alginate polymers of the alginate matrix contain more than 60% $\alpha$-L-guluronic acid. In some embodiments, one or more of the alginate polymers of the alginate matrix contain 60% to 80% $\alpha$-L-guluronic acid. In some embodiments, one or more of the alginate polymers of the alginate matrix contain 65% to 75% $\alpha$-L-guluronic acid. In some embodiments, one or more of the alginate polymers of the alginate matrix contain more than 70% $\alpha$-L-guluronic acid. In some embodiments, one or more of the alginate polymers of the alginate matrix contain more than 50% C-5 epimer $\beta$-D-mannuronic acid. In some embodiments, one or more of the alginate polymers of the alginate matrix contain more than 60% C-5 epimer $\beta$-D-mannuronic acid. In some embodiments, one or more of the alginate polymers of the alginate matrix contain 60% to 80% C-5 epimer $\beta$-D-mannuronic acid. In some embodiments, one or more of the alginate polymers of the alginate matrix contain 65% to 75% C-5 epimer $\beta$-D-mannuronic acid. In some embodiments, one or more of the alginate polymers of the alginate matrix contain more than 70% C-5 epimer $\beta$-D-mannuronic acid. Procedures for producing uronic blocks from are disclosed in U.S. Pat. No. 6,121,441. G-block alginate polymers and their uses as modulators of alginate gel properties is set forth in U.S. Pat. No. 6,407,226. Some preferred embodiments, 30% G, 35% G, 40% G, 45% G, 50% G, 55% G, 60% G, 65% G, 70% G, 75%, 80% G or 85% G.

The average molecular weight of alginate polymers affects gelling time, pore size, gel strength and elasticity of gels. Alginate polymers may have average molecular weights ranging from 2 to 1000 kD. The molecular weight of alginates may affect gel formation and the final gel properties. Generally, the lower the molecular weight of the alginate used the more biodegradable a gel will be. The alginate polymers or combinations thereof used in the soluble alginate components may be the same or different from the polymers or combinations thereof used in the insoluble alginate/gelling ion particles. In some embodiments, the alginate polymers of the alginate matrix have an average molecule weight of from 5 to 350 kD. In some embodiments, the alginate polymers of the alginate matrix have an average molecule weight of from 2 to 100 kD. In some embodiments, the alginate polymers of the alginate matrix have an average molecule weight of from 50 to 500 kD. In some embodiments, the alginate polymers of the alginate matrix have an average molecule weight of from 100 to 1000 kD. In some embodiments, gels are designed to have a high degree of biodegradability. Accordingly, gels having less alginate, less gelling ion lower G content and lower molecular weight alginates can be produced using the lower limits of one or more of these parameters as set forth herein to produce gels with a high degree of biodegradability.

The alginate may possess a viscosity in a 1% solution measured at 20 degrees centigrade of from 25 to 1000 mPas and in some embodiments, preferentially 50 to 1000 mPas (1% solution, 20 C).

In some embodiments, it is preferred that methods of manufacture of insoluble alginate/gelling ion particles provide products with stoichiometric amount (100% saturation) of gelling ion. Use of such stoichiometric salts imparts greater reproducibility in the self-gelling alginate systems. In some embodiments, it is preferred that method of manufacture of insoluble alginate/gelling ion particles provide products with sub-stoichiometric amount (<100% saturation) of said gelling ion. Use of such sub-stoichiometric salts imparts biodegradability to self-gelling alginate systems.

In some embodiments, the alginate is ultrapure alginate. Ultrapure alginate is commercially available such as from different sources of seaweed like *Laminaria Hyperborea*. Commercial calcium salts of alginic acid are generally manufactured in processes whereby calcium is added to alginic acid in the solid phase by simple admixture and kneading of the components together. Examples of commercially available calcium salts of alginic acid are Protaweld (from FMC BioPolymer) and Kelset from ISP Corporation. The insoluble alginate/gelling ion particles may be produced using ultrapure alginate by making an alginate gel using the ultrapure alginate and a gelling ion, washing out sodium or other ions that were present in the ultrapure alginate, drying the gel to remove the water, and making particles from the dried gel. In some embodiments, the insoluble alginate/gelling ion particles are stoichiometric salts. Insoluble alginate/gelling ion particles preferably have a high purity and a specific, consistent and generally uniform content of gelling ion such as, for example, calcium or strontium barium, zinc, iron, manganese, copper, lead, cobalt, nickel, or combinations thereof, such that gel formation speed and gel strength can be provided with more precise predictability. Insoluble alkaline earth salts of alginic acid such as for example calcium alginate or strontium alginate (depending upon the gelling ion used) or insoluble transition metal salts of alginic acid (such as those using gelling ions of copper, nickel, zinc, lead, iron, manganese or cobalt) can be manufactured with a known and pre-determined content of alkaline earth ions by precipitation from the solutions. In some embodiments, commercially available sodium alginate is first used to prepare a sodium alginate solution. Optionally, sodium salt such as sodium carbonate may be included in the sodium alginate solution. A salt containing the desired gelling ion for the insoluble alginate/gelling ion particle, such as for example, calcium salt or strontium salt such as calcium chloride or strontium chloride, is used to make a solution. The sodium alginate solution is combined, preferably slowly, with the gelling ion solution. Preferably, the combined solutions are continuously stirred during the mixing process. Insoluble alginate such as for example calcium alginate or strontium alginate (depending upon the gelling ion used) precipitates from the combined solutions. The precipitated insoluble alginate is then be removed from the solution and washed repeatedly, such as 2-10 times, with purified water for example to remove all soluble ions. The removal of soluble ions is confirmed for example by testing the conductivity of insoluble alginate in purified water compared to the conductivity of purified water. After washing, the insoluble alginate can be dried, such as with a vacuum. The dried alginate can be milled and, in some embodiments, selected for particle sizes.

In some embodiments, the alginate is sterile. In some preferred embodiments, the alginate is sterile ultrapure alginate. Conditions often used to sterilize material can change the alginate, such as decrease the molecular weight. In some embodiments, the sterile alginate is produced using sterility filters. In some embodiments, the alignate has an endotoxin level of <25 EU/gram.

In some embodiments, the alginate matrix is may be coated with a polycationic polymer like a poly amino acid or chitosan after the gel matrix forms. In some embodiments, poly-lysine is the polycationic polymer. In some embodiments, poly-lysine is linked to another moiety and the poly-lysine is thus used to facilitate association of the moiety to the gel. Examples of moieties linked to the gel using polycationic polymers include, for example, drugs, peptides, contrast reagents, receptor binding ligands or other detectable labels. Some specific examples include vascular endothelial growth factor (VEGF), epidermal growth factor (EGF), transforming growth factor (TGF), and bone morphogenic protein (BMP). Drugs may include cancer chemotherapeutic agents such as Taxol, cis-platin and/or other platinum-containing derivatives. Carbohydrate polymers may include hyaluronan, chitosan, heparin, laminarin, fucoidan, chondroitin sulfate. In some embodiments, the alginates used are modified alginate polymers such as chemically modified alginate in which one or more polymers are linked to a different alginate polymer. Examples of such modified alginate polymers may be found in U.S. Pat. No. 6,642,363, which is incorporated herein by reference.

In some embodiments, the alginate polymer may include a non-alginate moiety such as, for example, a drug, a peptide, a contrast reagent, a receptor binding ligand or other detectable label. In one embodiment, the alginate polymer includes an RDG peptide (Arg-Asp-Gly), a radioactive moiety (e.g. $^{131}$I) or a radio opaque substance. Other examples of moieties linked to alginate polymers include, for example, drugs, peptides, contrast reagents, receptor binding ligands or other detectable labels. Some specific examples include vascular endothelial growth factor (VEGF), epidermal growth factor (EGF), transforming growth factor (TGF), and bone morphogenic protein (BMP). Drugs may include cancer chemotherapeutic agents such as Taxol, cis-platin and/or other platinum-containing derivatives. Carbohydrate polymers may include hyaluronan, chitosan, heparin, laminarin, fucoidan, chondroitin sulfate.

The soluble alginate may be a salt such as, for example, $Na^+$-alginate, $K^+$-alginate, PEG-alginate (polyethylene glycol-alginate), $NH_4$-alginate or combinations thereof.

In some embodiments, the soluble alginate is freeze dried or otherwise desicated. Freeze dried soluble alginate is "immediately soluble." "Immediately soluble" alginate is soluble in water in less than one minute, preferably less than 30 seconds, more preferably less than 15 seconds. "Readily soluble" alginate takes more than one minute and usually several minutes to go into solution.

The gelling ions used in the insoluble alginate/gelling ion particles affects gelling kinetics, gel strength, and elasticity. Gelling ions also have affects on cell growth. The gelling ions used in the insoluble alginate/gelling ion particles may be $Ca^{++}$, $Sr^{++}$, $Ba^{++}$, $Zn^{++}$, $Fe^{++}$, $Mn^{++}$, $Cu^{++}$, Pb, Co, Ni, or combinations thereof.

The insoluble alginate gelling ion complexes are particles. The particles are generally non fibrous based on a L/D ratio where the particle shape is characterized by a largest dimension (L) and smallest dimension (D). Non-fibrous L/D is less than 10, preferably less than 5, preferably less than 2. An L/D of 10 or more is a chopped fiber. The insoluble alginate gelling ion can be maintained as a dispersion or in dry form. If the former, the dispersion can be mixed with a solution containing soluble alginate or with immediately soluble alginate to form a dispersion of insoluble alginate/gelling ion particles in a solution containing soluble alginate. If the insoluble alginate gelling ion particles are in dry form, they may be mixed with dry immediately soluble alginate and subsequently with a solution to form a dispersion of insoluble alginate/gelling ion particles in a solution containing soluble alginate or the dry insoluble alginate gelling ion particles may be combined with a solution containing soluble alginate to form a dispersion of insoluble alginate gelling ion particles in a solution containing soluble alginate.

The agitation that occurs upon mixing the components to form the dispersion results in distribution of the solid particles within the solution. The dispersion so produced can be in the form of a slurry which can be poured, injected and otherwise self gel within a mold or cavity to form the shape of such mold or cavity.

The dispersion of insoluble alginate gelling ion particles in a solution containing soluble alginate is formed, it is dispensed to the site where the self gelling occurs to form an alginate gel. In some embodiments, the dispersion is dispensed to a site in vivo. In some embodiments, the dispersion is dispensed on to a site on an individual's body. In some embodiments, the dispersion is dispensed into a mold or other container or surface.

The concentration of gelling ions used in the insoluble alginate/gelling ion particles affects gelling kinetics, gel strength, and elasticity. The higher the concentration of gelling ions, the higher the gel strength. Gel strength is highest when the gel is saturated with gelling ion. Conversely, the lower the concentration of gelling ion, the lower the gel strength and higher the degree of biodegradability.

The particle size of the insoluble alginate/gelling ion particles may affects gelling kinetics and the final properties of the gel. The smaller the particle size the more rapid the completion of gel formation. Larger particle sizes produce stronger gels. Particle sizes may be controlled by, for example, sifting insoluble alginate/gelling ion particles through various different size filters such that the particles can be generally all be within a predetermined size range. In some embodiments, particles are <25 µm, 25-45 µm, 45-75 µm, 75-125 µm or >125 µm.

The solvent used may be, for example, water, saline, sugar solution, cell culture solution, a solution such as a drug solution, protein, or nucleic acid solution, a suspension such as a cell suspension, liposomes, or a contrast reagent suspension.

The alginate hydrogel formed may comprise, for example, drugs nucleic acid molecules, cells, multicellular aggregates, tissue, proteins, enzymes, liposomes, a contrast reagent or a biologically active material. Examples of a biologically active material are hyaluronate and chitosan. Contrast reagents include tantalum and gadolinium. Some specific examples of proteins include vascular endothelial growth factor (VEGF), epidermal growth factor (EGF), transforming growth factor (TGF), and bone morphogenic protein (BMP). Drugs may include cancer chemotherapeutic agents such as Taxol, cis-platin and/or other platinum-containing derivatives. Carbohydrate polymers may include hyaluronan, chitosan, heparin, laminarin, fucoidan, chondroitin sulfate.

The cells that can be used in the gels include non-recombinant and recombinant cells. In some embodiments in which cells are encapsulated within an alginate matrix, encapsulated cells are mammalian cells, preferably human cells. In some embodiments in which encapsulated cells are non-proliferating cells, the non-proliferating cells may be selected from the group consisting of: pancreatic islets, hepatic cells, neural cells, renal cortex cells, vascular endothelial cells, thyroid and parathyroid cells, adrenal cells, thymic cells, ovarian cells and chondrocytes. In some embodiments in which encapsulated cells are proliferating cells, the proliferating cells may be stem cells, progenitor cells, proliferating cells of specific organs, fibroblasts and keratinocytes or cells derived from established cell lines, such as for example, 293, MDCK and C2C12 cell lines. In some embodiments, encapsulated cells comprise an expression vector that encodes one or more proteins that are expressed when the cells are maintained. In some embodiments, the protein is a cytokine, a growth factor, insulin or an angiogenesis inhibitor such as angiostatin or endostatin, other therapeutic proteins or other therapeutic molecules such as drugs. Proteins with a lower MW, less than about 60-70 kD, are particularly good candidates because of the porosity of the gel-network. In some embodiments, the cells are present as multicellular aggregates or tissue.

Self gelling alginates may be used to produce alginate gels greater than 5 mm with a homogenous alginate network. In some embodiments, the homogenous alginate gel is greater than 10 mm. The gel formed by the diffusion methods are generally not homogenous alginate gels greater than 1 mm. In preferred embodiments, the homogenous alginate gel formed by self gelling alginate gel formation is free of sulfates, citrates, phosphates (TSPP: Tetra sodiumPyroPhosphate and Polyphosphate are used in food applications with alginate puddings etc.), lactates, EDTA (Ethylenediaminetetra-acetic acid) and lipids as with liposomes used to encapsulate gelling ion.

There are numerous applications for self-gelling alginate. In some embodiments, the self-gelling alginate is used in food products. The self-gelling alginates that are particularly useful in those food products which are prepared as a liquid/slurry mixture with other food ingredients and is dispensed into a vessel. The vessel is preferably a mold where the gel/food product sets to form a solid or semi-solid with a molded shape. Candies, edible decorations, puddings and other molded shape food products can be prepared.

In some embodiments, the self-gelling alginates are used in biomedical applications. Biocompatible self-gelling alginates may be applied topically. The biocompatible self-gelling alginates are particularly useful in those biomedical applications in which it is desired for the gel matrix to conform to a space in situ such that the self-gelling alginate can be dispensed as a dispersion into the site where the matrix is desired. The dispersion fills the cavity or space in liquid/slurry form and sets to form a solid within the cavity or space. Alternatively, the dispersion be dispensed topically where it can be spread prior to setting. In some embodiments, the self-gelling alginates are used in the manufacture of matrices which can be prepared with specific shapes by preparing a liquid/slurry mixture that is dispensed into a mold where it sets to form a solid with a molded shape and/or to prepare matrices with encapsulated cells useful as tissue or organ replacements.

Alginate self-gelling systems that are controllable, biocompatible and particularly designed for in situ gel formation implantation purposes are provided. Solutions that can easily be used for injections or applied in other ways inside or outside the body are provided which set to form solid gel matrices. By mixing an alginate in the presence of a solvent with a gelling ion source of which the gelling ions are bound within the gel network of an insoluble particle, the gel forming material can be dispensed as a liquid and set in a desirable pattern and time frame. The solution at a predefined time hardens and forms a gel. The formulation is biocompatible, as variations in pH and presence of toxic compounds are omitted. Significant deviations from biologic pH are unnecessary.

In some embodiments, the self gelling alginate is used in biomedical applications such as tissue bulking such as for the treatment of reflux problems (i.e. treatment of incontinence, renal reflux or esophageal reflux problems), embolization such as in the treatment of benign or malignant tumors, anti-adhesion treatment as post-surgical procedures, and wound treatment. The current technology may be used in several applications, including tissue constructs ex vivo or in vivo, as cells or other biomaterials may be mixed into the gelling system thereby creating a bioartificial extracellular matrix supporting cells or tissue. According to some applications, biocompatible solid depots may be implanted which release active ingredients such as proteins and drugs over time.

The self gelling alginate is particularly useful as a tissue bulking material in that it can be introduced to a site that is remotely accessible and dispensed as a liquid slurry to more fully conform to a cavity relative to other types of implants. The dispersion can be dispensed in an amount sufficient to displace and support other tissues or organs in the body and upon formation of a gel in situ provide structure to maintain and support the other tissue or organs. The self gelling alginate may comprise components that make it well suited for tissue bulking applications. For example, the use of strontium as a gelling agent will result in a gel that inhibits cell overgrowth and unwanted tissue formation.

The self gelling alginate is particularly useful in embolization procedures in that it can be introduced to a blood vessel that is remotely accessible and dispensed as a liquid slurry to fully conform to interior or the blood vessel and more fully and effectively block it off relative to other types of closures such as sutures. The dispersion can be dispensed in an amount sufficient to block off circulation upon formation of a gel in situ. The self gelling alginate may comprise components that make it well suited for embolization applications. For example, the components can be selected for relatively fast setting and high strength. The self gelling alginate used in embolization applications may include contrast reagents to monitor its presence and location.

The self gelling alginate is particularly useful in anti-adhesion treatment as post-surgical procedures in that it can be introduced throughout the area of surgical intervention as a liquid slurry to fully cover exposed surfaces particularly at or near incision sites. The self gelling alginate may comprise components that make it well suited for anti-adhesion applications. For example, the use of strontium as a gelling agent will result in a gel that inhibits cell overgrowth and unwanted tissue formation.

The self gelling alginate is particularly useful wound treatment in that it can be introduced throughout the area of wound as a liquid slurry to fully cover exposed surfaces. In addition, the self gelling alginate can be dispensed internally through the wound site for example as a liquid slurry. The dispersion can be dispensed in an amount sufficiently to fill the internal cavity whereupon formation of a gel in situ the gel will block off any internal wounds and prevent blood loss through internal bleeding. The self gelling alginate may comprise components that make it well suited for wound treating applications. For example, blood clotting components as well as antiseptic and antibiotic compositions may be included.

The self gelling alginate is particularly useful to produce tissue constructs ex vivo or in vivo. Cells or other biomaterials may be mixed into the gelling system thereby creating a bioartificial extracellular matrix supporting cells or tissue. The dispersion can be introduced in situ as a liquid slurry to a site where the tissue/cells can function to achieve a therapeutic effect. Examples of tissue constructs include bone, cartilage, connective tissue, muscle, liver, cardiac, pancreas and skin. Examples of this may be preparations containing insulin-secreting cells for the treatment of diabetes, formulations containing chondrocytes for the repair of defective joints, and cells for treating Parkinson's disease. Such cells can be incorporated into the liquid slurry and dispensed into the site where upon gel formation they will exist and function within a biocompatible alginate matrix. The gel may also be used as an immune-barrier protecting entrapped cells against the host immune system. Self-gelling alginate may also be used to encapsulate cells ex vivo whereby the gel can be formed into a shape compatible with its intended use. In some embodiments, the self-gelling alginate may be used to encapsulate cells, such as dermal cells, and prepare artificial skin such as that which is used to treat burn victims and others in need of skin grafts or large area wound healing. In some embodiments, the self-gelling alginates may be used to encapsulate cells and form matrices which can be implanted.

The treatment of diabetes may comprise the production of a biocompatible matrix comprising insulin producing cells by preparing dispersion comprising insoluble alginate/gelling ion particles and insulin producing cells in a solution of soluble alginate and dispensing the dispersion to a site in an individual's body where the biocompatible matrix forms. The site within the individual body may be a cavity or a structure implanted within the individual. The dispersion may be dispensed into a mold, structure or container where is forms a biocompatible matrix which is implanted into the body of an individual. The insulin produced by the cells in the matrix is secreted by the cells and released from the matrix into the body of the individual where it functions to alleviate the symptoms of the diabetic condition. In some embodiments, the insulin producing cells are pancreatic islet cells. In some embodiments, the insulin producing cells are recombinant cells produced to express and secrete insulin.

The self gelling alginate is particularly useful to produce coated devices such as implantable devises. In some embodiments, the device is selected from the group consisting of: a stent, a cardiac pacemaker, a catheter, an implantable prosthetic, a surgical screw, a surgical wire, a tissue bulking implant, an esophagus reflux inhibiting implant, an incontinence inhibiting implant, a renal reflux, a container suitable for holding cells that are deposited on the exterior of a surface and/or encapsulated with an alginate matrix such as a solid device or macrocapsule, a breast implant, a chin implant, a cheek implant, a pectoral implant, a gluteus implant and a dental implant. The coating using self gelling alginate produces an effective coating regardless of shape. The use of strontium as gelling ion is particularly useful to inhibit cell overgrowth upon implantation.

Self-gelling alginates may be used in the manufacture of matrices which can be implanted. Such matrices can be prepared with specific shapes by preparing a liquid/slurry mixture that is dispensed into a mold where it sets to form a solid with a molded shape. Matrices prepared for implantation may comprise biologically active agents and/or cell. The gels may be produced and implanted surgically, applied topically or into an organ through external openings.

According to some embodiments, kits are provided for producing an alginate gel. The kits may comprise a first container comprising soluble alginate; and a second container comprising insoluble alginate/gelling ion particles. The individual containers may be separate container compartments of an integrated container system.

In some embodiments, the kits comprise soluble alginate in the form of a solution. In some embodiments, the kits comprise soluble alginate free of a solvent. In some embodiments, the kits comprise an additional container comprising a solvent.

In some embodiments, the kits comprise insoluble alginate/gelling ion particles in the form of a powder. In some embodiments, the kits comprise insoluble alginate/gelling ion particles in the form of a dispersion.

In some embodiments, the kits comprise an additional container comprising a drug, a peptide, a protein, a cell, a detectable label or a contrast reagent. In some embodiments, the kits comprise a drug, a peptide, a protein, a cell, a detectable label or a contrast reagent included in the container comprising soluble alginate solution or powder and/or in the container comprising insoluble alginate/gelling ion powder or dispersion.

According to some embodiments, compositions are provided for preparing a gel. The composition comprises an immediately soluble alginate and insoluble alginate/gelling ion particles. The composition may further comprise a drug, a peptide, a protein, a detectable label or a contrast reagent. The composition may be a component in a kit. Such a kit may further comprise a container with a solvent.

Kits preferably contains instructions for use.

In some embodiments, the kits comprise a mixing device. Mixing devices may be integrated as part of a container or container system. In some embodiments, the mixing device comprises a valve system which allows for passage of the dispersion from one container to a different container to facilitate mixing.

In some embodiments, the kits comprise a dispensing device. The dispensing device may be an applicator in communication with a mixing device and/or a container adapted for containing the dispersion. In some embodiments, the dispensing device comprises a catheter. In some embodiments, the dispensing device comprises a syringe.

EXAMPLES

Example 1

Gelling with Different Calcium Concentrations

In this experiment gels were made by mixing a solution of sodium alginate (Protanal SF 120) and a calcium alginate dispersion (Protaweld TX 120). The amount of calcium alginate was varied (1.0%, 1.5% or 2.0% in the gel), while the amount of sodium alginate was constant (1.0% in the gel). The setting of the self gelling system during time was measured by using a Physica MCR 300 rheometer (Measuring system: PP50, serrated, Temperature: 20° C., Gap: 1 mm, Frequency: 1 Hz, Strain: 0.005). The solution and dispersion were mixed immediately before addition of a 3 ml sample to the rheometer, and the oscillation test was performed over a period of 18-24 hours.

As shown in FIG. 1, the gel strength increased rapidly with time during the first 1-2 hours, and thereafter the change in gel strength was reduced as the gel showed a tendency to stabilize. The data also shows that the gel strength was increased at the higher calcium concentration.

Example 2

Gelling with Different Alginate Concentrations

Figure 2:
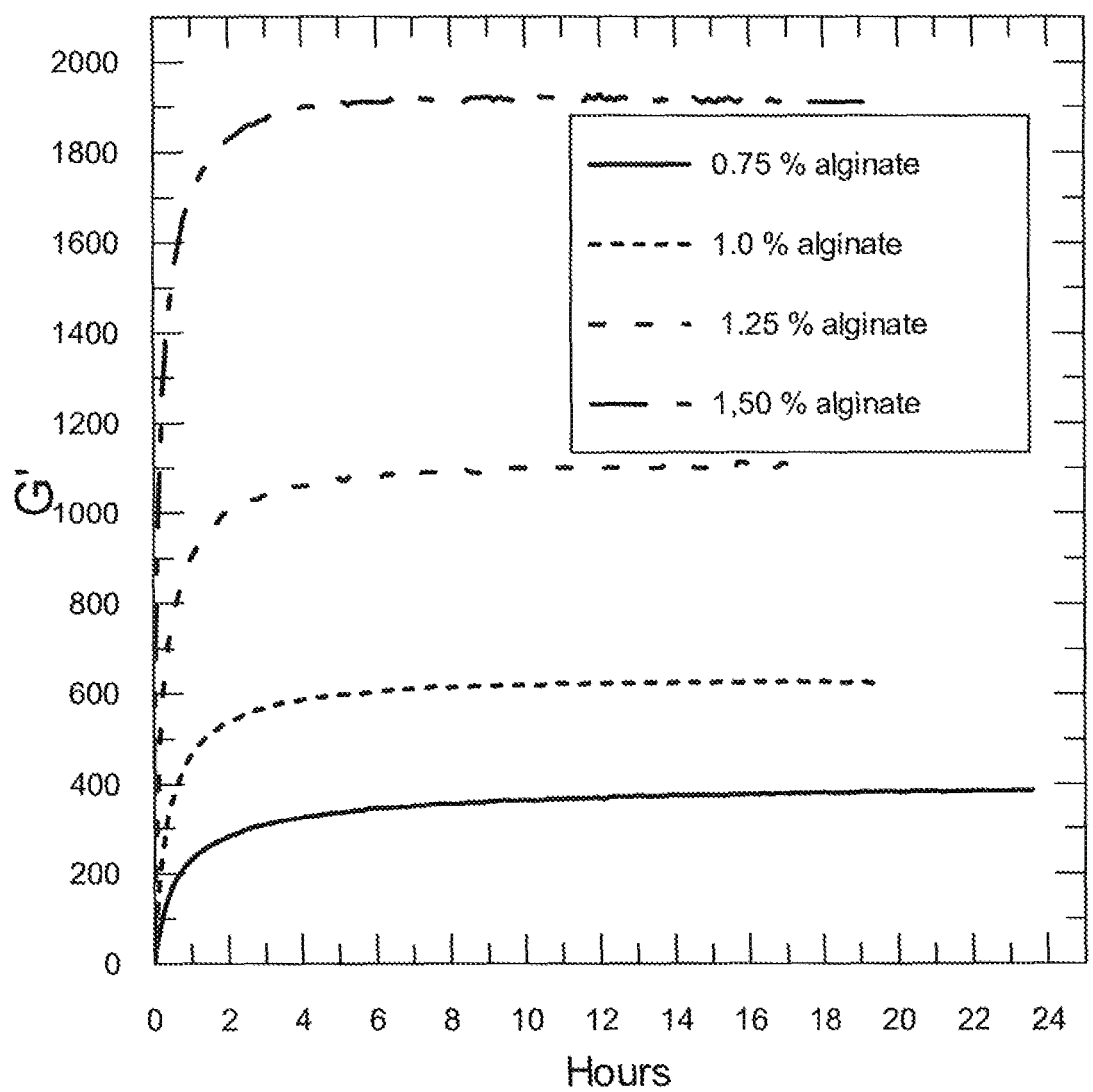
FIG. 2 contains data from rheometer measurements. Oscillation measurements were performed using a Physica MCR300 rheometer. Storage modulus as a function of time for gels made by mixing equal amounts of sodium alginate (Protanal SF 120) and calcium alginate (Protaweld TX 120) at the following concentrations in the gel: 0.75%, 1%, 1.25% or 1.5% sodium alginate and calcium alginate FIG. 3 contains data from rheometer measurements. Oscillation measurements were performed using a Physica MCR300 rheometer. Storage modulus was measured as a function of time for gels containing different molecular weights of calcium alginates (panel A) and sodium alginates (panel B) are shown as follows. The gels in panel A contain 1% sodium alginate and 1.5% calcium alginate and the gels in panel B contain 1% calcium alginate and 1% sodium alginate. The alginates used in panel A were: Calcium alginate: Protaweld TX 120 and Protaweld TX 120 degraded for 33 days at 60°. The viscosity (1% solution at 20° C.) of the two Ca-alginates, measured as sodium alginate, was 270 mPas and 44 mPas, respectively. Sodium alginate: Protanal SF 120. The alginates used in panel B were: Calcium alginate: Protaweld TX 120. Sodium alginate: Protanal SF 120 and Protanal SF/LF. The viscosity (1% solution at 20° C.) of the sodium alginates was 95 mPas and 355 mPas, respectively.

Alginate self gelling systems were made by mixing a solution of sodium alginate (Protanal SF 120) with a suspension of calcium alginate and measurements performed as described in Example 1. Oscillation measurements were made over a period of 18-24 hours. Equal amounts of sodium alginate (Protanal SF 120) and calcium alginate (Protaweld TX 120) were used. The amount of sodium alginate and calcium alginate was each adjusted to be 0.75%, 1%, 1.25% and 1.5% in the final gel respectively (FIG. 2). The gelling kinetics followed a similar pattern in all four cases. However, as in Example 1 the gel strength clearly increased with increasing alginate concentrations.

Example 3

Gelling with Alginates of Different Molecular Weight

Figure 3:
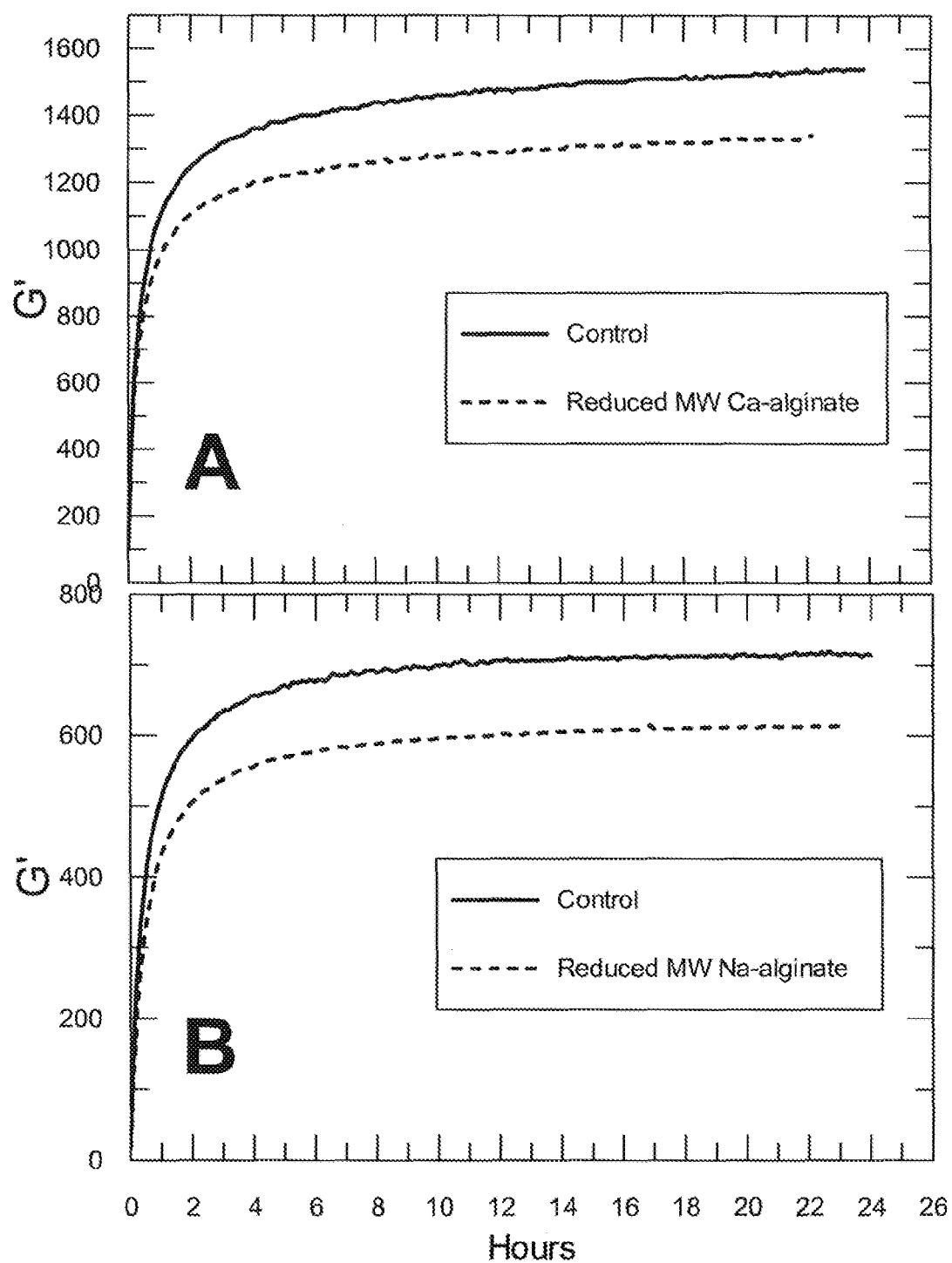
Figure 11:
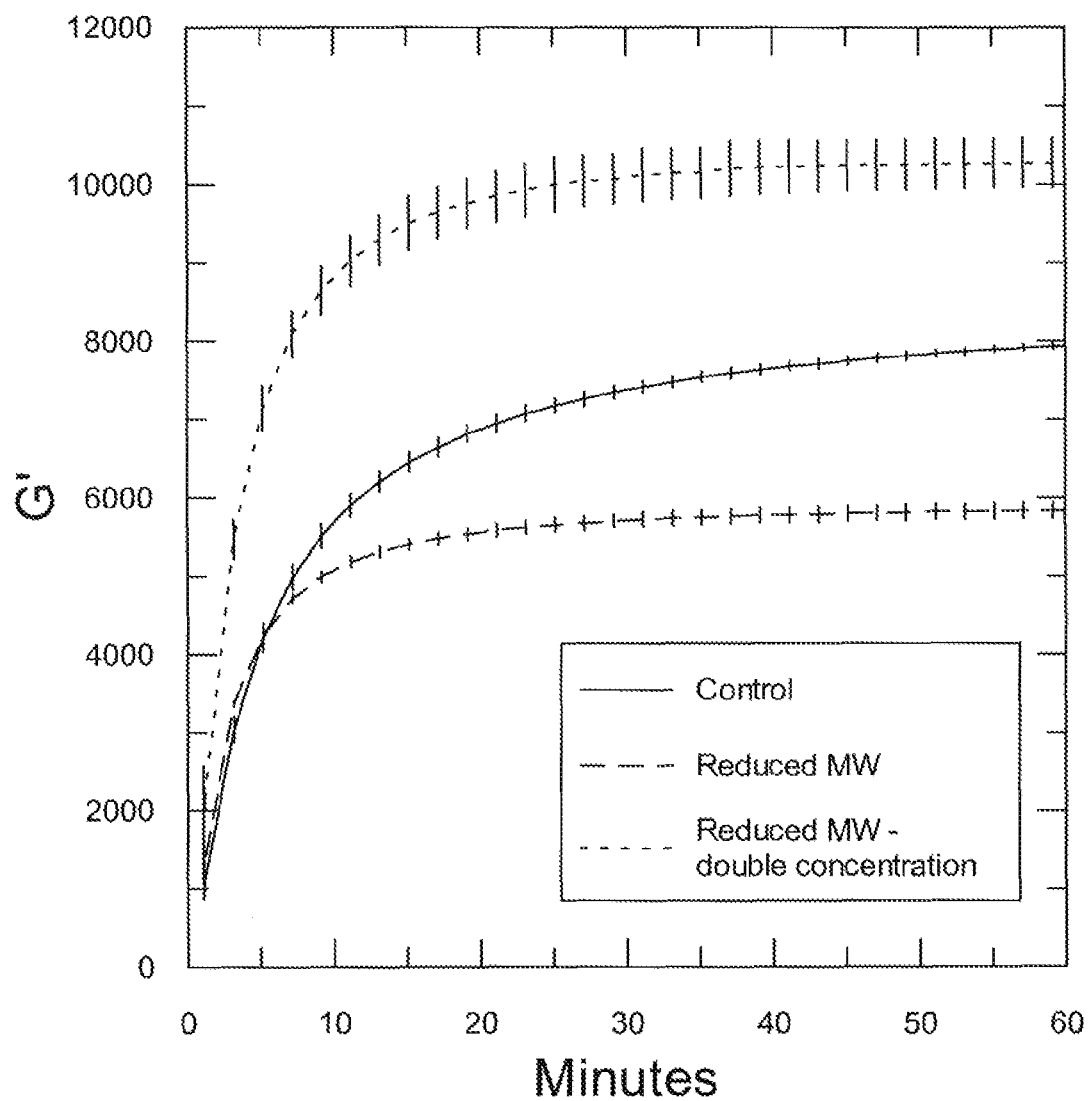
FIG. 11 contains data from rheometer measurements. Oscillation measurements were performed using a Physica MCR300 rheometer. Storage modulus was measured as a function of time for gels containing different molecular weights of sodium alginate. The gels contain 1.25% sodium alginate (PRONOVA UP100G) not degraded (control) or the same alginate batch degraded. A gel was also made of the degraded sodium alginate at a concentration of 2.5% (upper curve). In all cases the sodium alginates were mixed with 5.5% strontium alginate (Example 14) at a ratio of 4:1. Each curve is the mean of three independent measurements (curves) with standard error of the mean shown for each point.

In this experiment the gelling kinetics for sodium- and calcium alginates with different molecular weight was compared (FIG. 3). A reduced MW sample of the alginate (Protaweld TX 120) was obtained by increasing the temperature for several days (FIG. 3, Panel A) Protanal SF 120 and Protanal SF/LF sodium alginates with different MW were also compared (FIG. 3, Panel B). Rheological measurements were performed as described in Example 1 and the data are shown in FIG. 3. As shown in the figure the gelling process was clearly dependent upon the alginate molecular weight both for sodium and calcium alginate. In both cases the gel strength increased more rapidly for the high molecular weight alginate and also reached a higher level. Similarly to what is seen in FIG. 3, FIG. 11 also shows gelling of a reduced MW sample of sodium alginate (PRONOVA UP G 100) obtained by increasing the temperature. However, in this case gelling was initiated by mixing with strontium alginate. As shown in FIG. 11 the gelling process was clearly dependent upon the alginate molecular weight as the gel strength reached a higher level for the high molecular weight alginate. The data FIG. 11, which used calcium alginate or strontium alginate at 100% saturation stoichiometry, also shows that increasing the alginate concentration may compensate for the reduction in MW with regards to gel strength.

Example 4

Gelling with Different Gelling Ions

Figure 4:
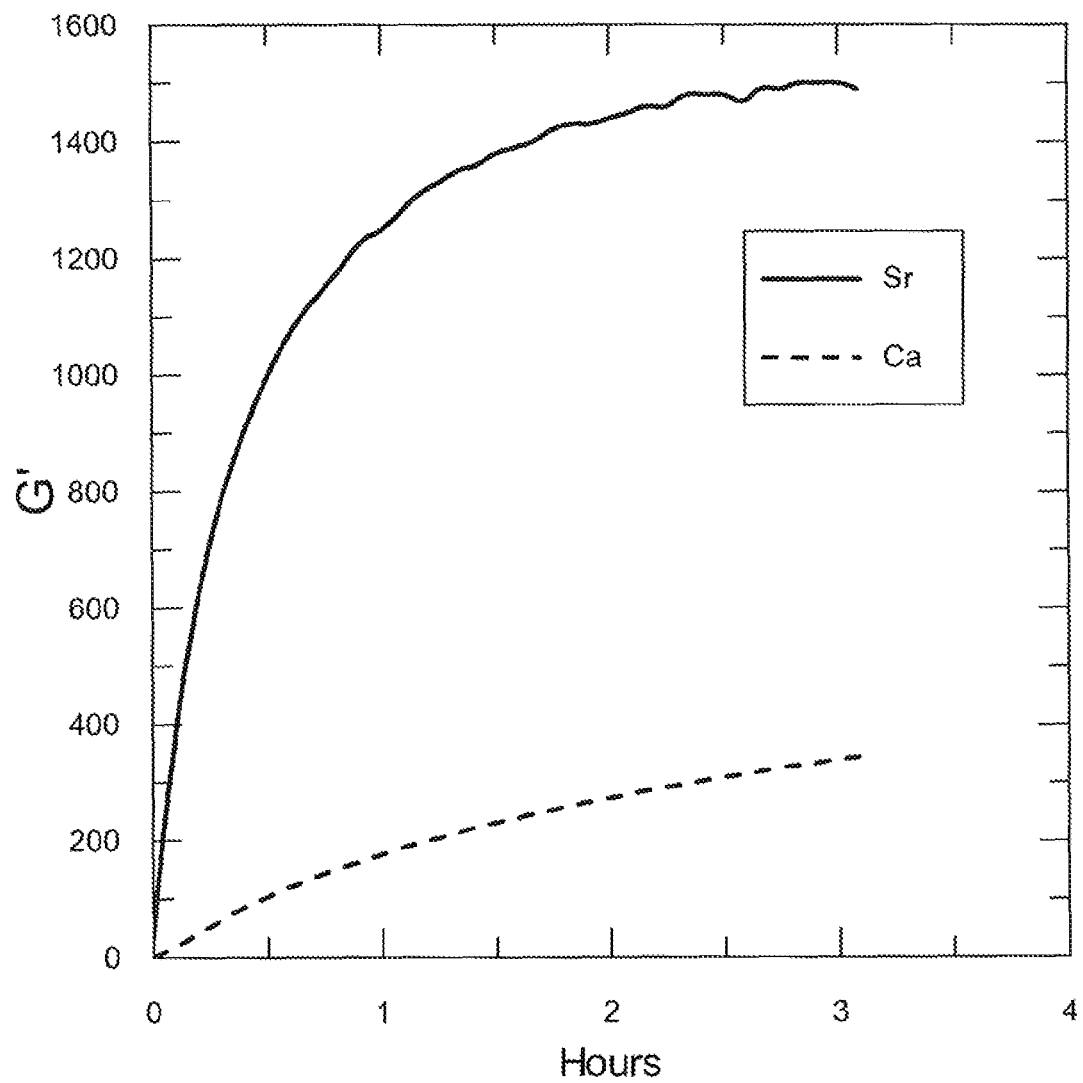
FIG. 4 contains data from rheometer measurements. Oscillation measurements were performed using a Physica MCR300 rheometer. Storage modulus as a function of time for gels made with strontium or calcium as gelling ions. The amount of sodium alginate (Protanal SF 120) and strontium/calcium alginate was each adjusted to be 0.75% in the gel. The calcium alginate used was made by kneading alginic acid (FMC process product) (65.2 g) with calcium carbonate (35.32 g) in a lab kneader for 1 hour, then drying and milling. The strontium alginate used was made by kneading alginic acid (FMC process product) (65.2 g) with strontium carbonate (52.10 g) in a lab kneader for 1.5 hour, then drying and milling.

In this experiment calcium or strontium alginate was mixed with sodium alginate (Protanal SF 120). Calcium and strontium alginates were made by kneading alginic acid with calcium carbonate. Rheological measurements were performed as described in Example 1 and the data are shown in FIG. 4. The amount of sodium alginate and strontium/calcium alginate was each adjusted to be 0.75% in the gel. Clearly, the use of strontium as gelling ion gave rise to a stronger gel structure as well as a faster gelling kinetics.

Example 5

Gelling with Different Content of Guluronic Acid

Figure 5:
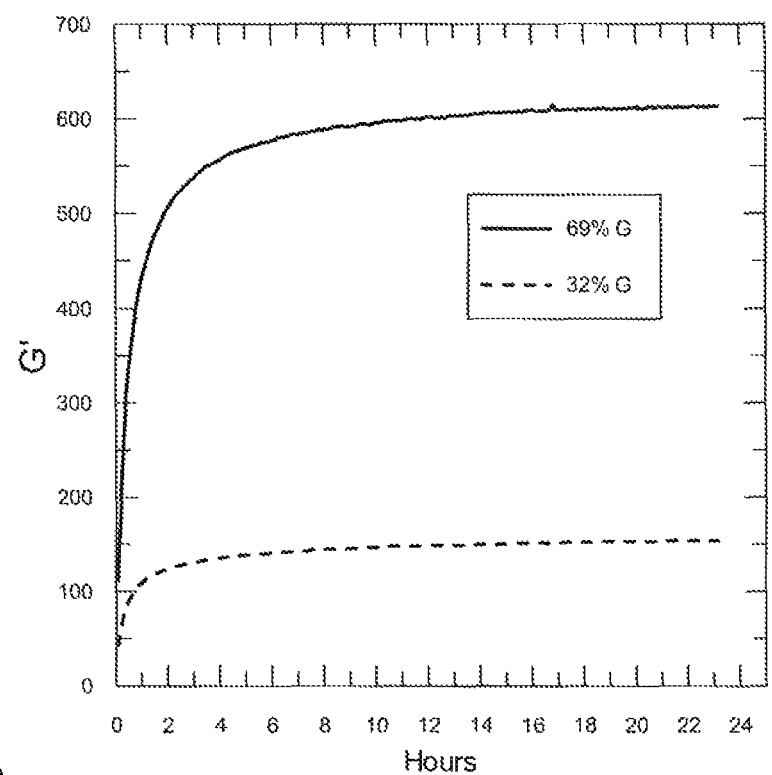
FIG. 5 contains data from rheometer measurements. Oscillation measurements were performed using a Physica MCR300 rheometer. Storage modulus as a function of time for gels containing sodium alginate with high and low content of guluronic acid.
Figure 5:
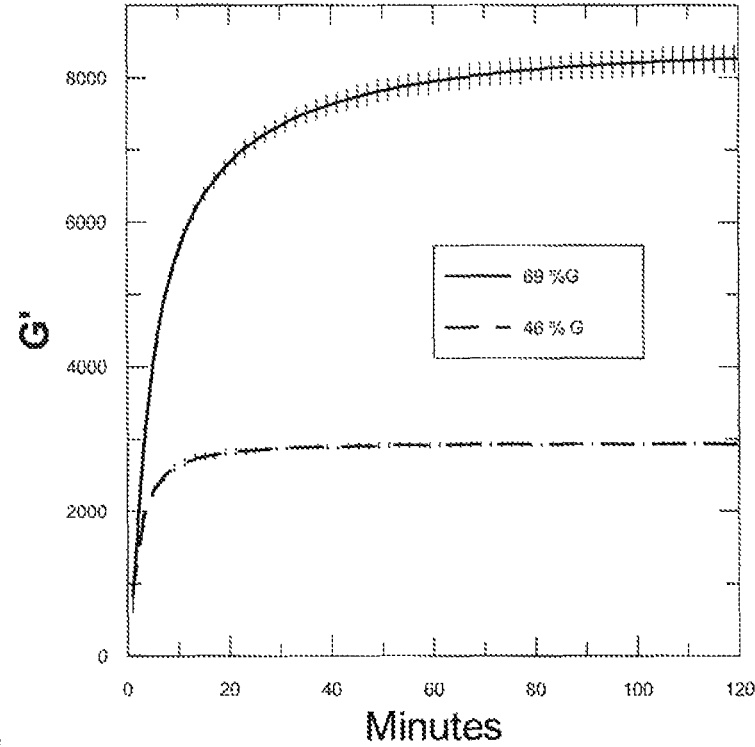

As the content of guluronic acid in alginates are known to have major influence on the gel strength of alginate gels the effect of using sodium alginates (Protanal SF 120 and Protanal HF 60D) with different content of guluronic acid was tested. In FIG. 5, panel A is shown the storage modulus as a function of time for gels containing sodium alginate with a high or low content of guluronic acid. In both curves the system was gelled by mixing with a dispersion of calcium alginate (Protaweld TX 120) with a high content of guluronic acid. The amount calcium alginate and sodium alginate used was adjusted to be 1.0% of each in the gel. Measurements were performed as described in Example 1. Clearly the use of a sodium alginate with a high content of gluronic acid increased the gel strength of the system although in both cases a calcium alginate with a high content of guluronic acid was used. In FIG. 5, panel B, strontium alginate (FMC process product with a high content of guluronic acid per Example 14) was also mixed with sodium alginates with a high and low content of guluronic acid. The sodium alginates used were PRONOVA UP 100G (69% G, MW: 122 000) and PRONOVA UP 100M (46% G, MW: 119 000). The MW (and viscosity) of the two sodium alginate batches was selected to be similar (as close as possible). As the data clearly shows, also when using strontium alginate as the gelling ion source, the use of sodium alginate with a high content of guluronic acid increased the gel strength compared to a sodium alginate with a low content of guluronic acid.

Example 6

Figure 6:
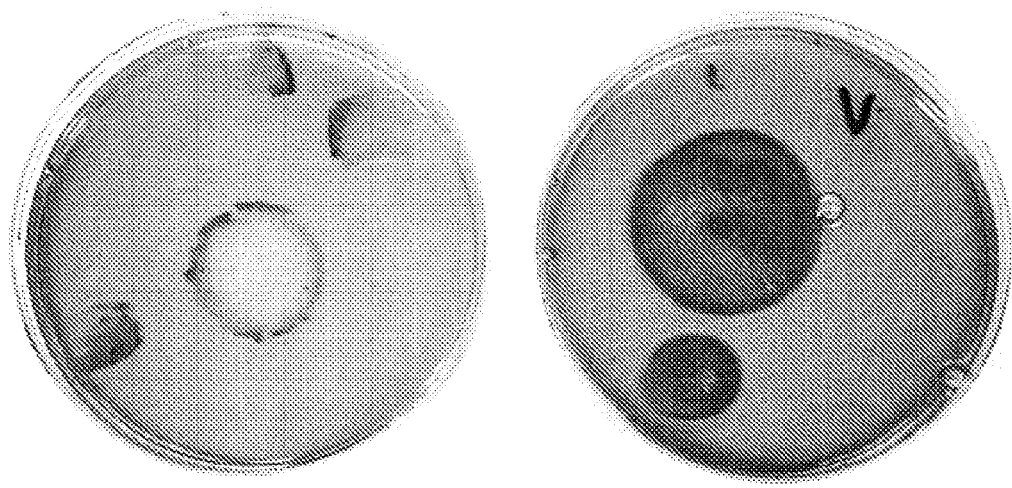
FIG. 6 shows stability and biodegradability for alginate gels made with different content of calcium ions and stored for 6 months under physiologic conditions. Gels discs were made by mixing an autoclaved calcium alginate dispersion (Protaweld TX 120) and sterile filtered sodium alginate (PRONOVA UP LVG) to a final concentration of 1.0% alginate each and the dispersion was gelled in the two Petri dishes. The gel discs in one dish (marked V) was washed with 50 mM calcium chloride for 10 minutes after gelling and both dishes was thereafter added cell culture medium (DMEM supplemented with 10% FBS). The dishes were stored under sterile conditions in a $CO_2$-incubator and the medium was changed regularly three times a week. The size of the largest gel disc in each dish was initially of the same size. The picture shown was taken after six months.

Stability of Gels Made with Different Calcium Content Under Physiologic Conditions In this example, stability and biodegradability of alginate gels made with different content of calcium ions was observed (FIG. 6). Gels discs were made by mixing calcium alginate (Protaweld TX 120) autoclaved for sterility and a sterile filtered sodium alginate (Pronova UP LVG) to a final concentration of 1.0% and 0.7% respectively. The dispersions was gelled into two Petri dishes. The gel discs in one dish (marked V) was after initial gelling washed with 50 mM calcium chloride for 10 minutes and both dishes was thereafter added cell culture medium (DMEM supplemented with 10% FBS). The medium in the dishes was then changed with fresh medium regularly three times a week and the dishes were stored in a $CO_2$ incubator at 37° C. under sterile conditions. The initial size of the largest gel disc in each dish was of the same size. After six months a major fraction of the gel not washed with calcium as shown in FIG. 6 disappeared while the gel discs washed with additional calcium remained with little or no change in size during time. This clearly shows that the alginate gel made with a limited content of calcium may be strongly degraded under physiologic conditions.

Example 7

Cell Entrapment

Encapsulation of cells in alginate microbeads is a widely used technique currently under development for different biomedical applications. Alginate beads are used as a "biofactory" for therapeutic substances. The alginate gel allows the influx of essential nutrients like oxygen and glucose and the efflux of desired therapeutic molecules and waste products. By using responsive cells like islet cells the "biofactory" responds to the host. However, the gel network needs to protect the entrapped cells from the immune system of the host which is highly critical when implanting foreign cells into the body. It has, however, been shown that cells may be successfully entrapped in other alginate structures than microbeads.

Figure 7:
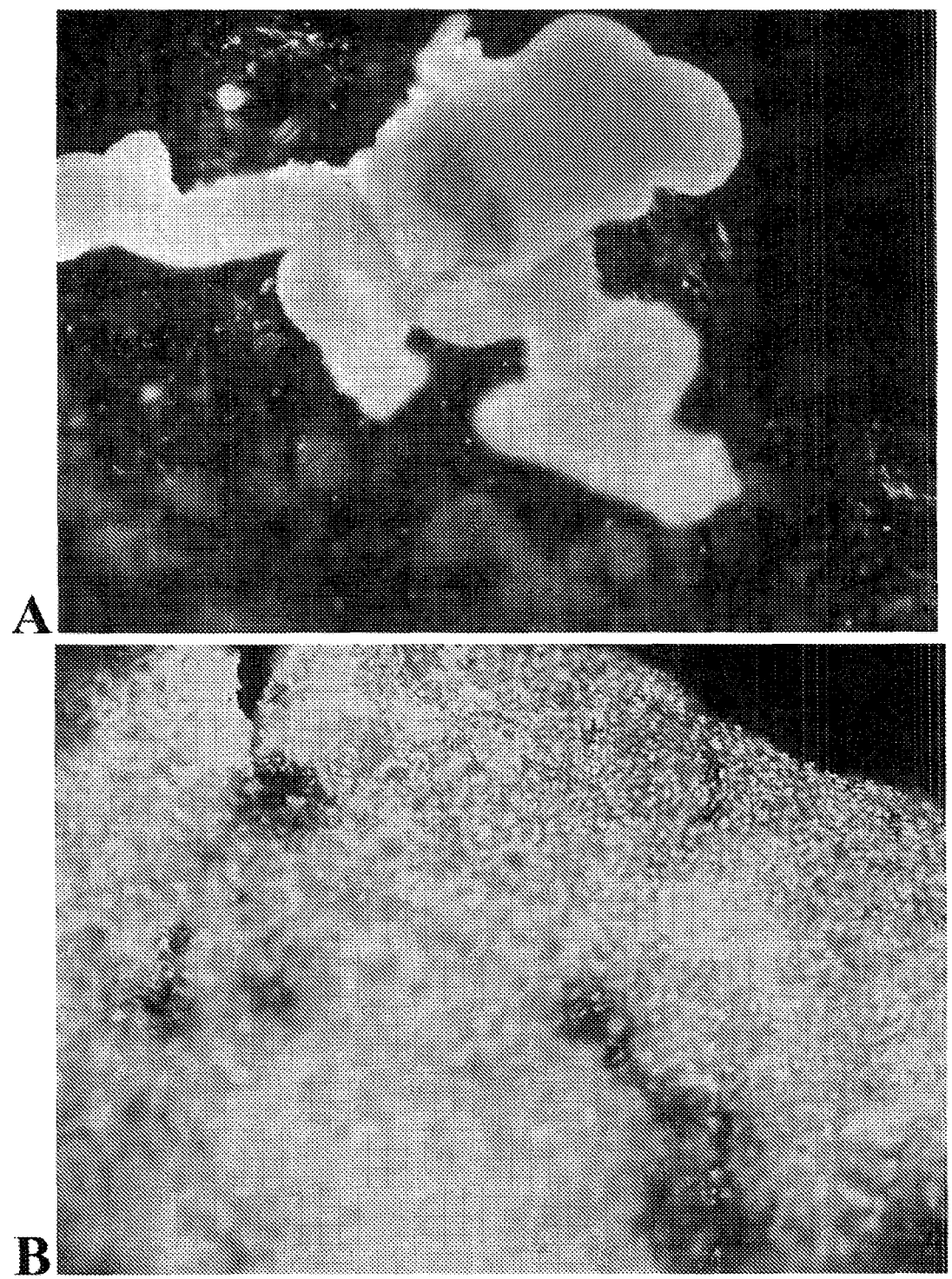
FIG. 7 shows data from experiments using cells entrapped in alginate self-gelling alginate.

The effect of the gel on cells entrapped in our self gelling alginate matrix are also shown (FIG. 7). In one of the experiments (FIG. 7, panel A) C2C12 mouse myoblast cells were mixed with PRONOVA UP MVG alginate solution before mixing with an autoclaved calcium alginate dispersion (Protaweld TX 120). The mixture containing cells and 0.7% sodium alginate and 1.0% calcium alginate was injected into a Petri-dish and molded as disks. After a few minutes the gel was washed with 50 mM calcium chloride for 10 minutes in order to prevent degradation of the gel (see Example 6) and the cell growth medium (DMEM supplemented with 10% FBS) was thereafter added to the gel. The alginate gel/cell culture was stored in a $CO_2$-incubator at 37° C. under sterile conditions and the medium was thereafter regularly changed three times a week. After 45 days in culture the presence of viable cells were visualized under microscope by calcein staining. A fluorescence microscope was used to visualize living cells.

The picture shown in FIG. 7, panel A, shows the presence of viable cells both outside and inside the gel. Because of different focusing in the microscope on different part of the gel different spots are more or less clear in the picture. Numerous viable cells or small cell colonies can be seen inside the gel as small enlightened spots. The large enlightened area covering a large part of the picture shows viable cells that has entered the gel surface and multiplied there. This part of gel surface is covered completely with cells growing as monolayers. Some cell aggregates on the gel surface are, however, also present in other areas.

In another experiment (FIG. 7, panel B) human chondrocytes were entrapped in alginate self-gel. In this case the gel was made of 5 ml mixed self-gel of PRONOVA SLG 20 (low viscosity lyophilized sterile alginates with high guluronic acid content) and calcium alginate (FMC process product, Example 14) containing human chondrocytes. Three days after gelling the gel was sectioned into 600 µm slices using a vibratome. The gel slices was stored in cell growth medium in a $CO_2$-incubator and the picture was taken after six months. The picture was taken using a fluorescence microscope after staining the cells with calcein as an indicator of cell viability. The picture clearly demonstrates the presence of a high number of viable cells. The alginate gel network therefore must be a good matrix in supporting the cells for a long period of time. In conclusion the data clearly demonstrates that the gel may be a biocompatible matrix for cells and cell growth.

A series of different alginate samples containing human chondrocytes were also prepared. In this case higher molecular weight alginates were selected in order to retain gel strength at low gelling ion and alginate concentrations. These were PRONOVA SLG 100 and PRONOVA SLM 100 (high viscosity lyophilized sterile alginates with high and low guluronic acid content respectively). Chondrocytes were mixed into an approximately 2% solution of alginates in cell medium. The alginate/cell suspensions were then maintained for about half an hour in order to allow release of air bubbles before further use. The cells suspensions were then mixed with insoluble calcium or strontium sterile alginates (FMC process product prepared per Example 14, in vials containing 5 ml 10% alginate dispersion, totally 0.5 mg alginate). Each vial of insoluble alginate contained a magnet for stirring and was used on the same day after opening. The insoluble products had also been milled and sifted in order to control the particle size and were manufactured as strontium and calcium alginates with a high or low guluronic acid content. The mixing of the alginate/cell suspension and insoluble alginate dispersion were done in small volumes in small test tubes. The insoluble alginate dispersions were kept under magnet stirring when the desired volumes were taken out of the vials. Different samples were mixed as described in the table below.

| Gel systems containing cells (start concentrations in parenthesis) | | | |
|---|---|---|---|
| Group | Alginate solution | Ions source alginates | Mixing |
| Alt. 1 | 1.6% PRONOVA SLG 100 (2.0%) | 2.0% Strontium high G (10%) | 4:1 |
| Alt. 2 | 1.6% PRONOVA SLG 100 (2.0%) | 2.0% Calcium high G (10%) | 4:1 |
| Alt. 3 | 1.6% PRONOVA SLM 100 (2.0%) | 2.0% Strontium high G (10%) | 4:1 |
| Alt. 4 | 1.6% PRONOVA SLG 100 (2.0%) | 2.0% Strontium high M (10%) | 4:1 |

After an initial gelling of the mixture for a few minutes the small gel pieces were stored in the cell culture medium in a $CO_2$ incubator and cell viability was checked with calcein staining (as previously described) after a week. In this study, good cell viability in all the alginate gel/cell samples was observed. Alternatively, alginate/chondrocyte samples can be prepared in situ. Depending on the application, different self-gel formulations may be adapted for each particular use. The gel may contain cells directly but may also contain microbeads or other biostructures containing cells. The formulation may be injected before the gelling has completed but the gel could also be allowed to set ex vivo, either completely or partially before implantation. Furthermore, the gel may be made more or less strong or porous in order to allow cell proliferation within the gel or not, to adapt to the environment or give immunoprotection. Depending of the type of gelling ion and type of alginate the gel can be formulated to be less attractive for the overgrowth of cells. Also the gel structure may be made more or less biodegradable by using a low calcium content (as shown in Example 6 and FIG. 6), low molecular weight alginate or low alginate concentrations. The gel may also be mixed with other biopolymers like hyaluronate or chitosan for improved properties. The gel may also be further strengthened by applying additional calcium to the construct through a suitable soaking or spraying procedure.

Example 8

Controlled Release Systems

The usefulness of alginate in controlled release systems for the delivery of drugs or other therapeutic molecules has been demonstrated. The type of gel preparations demonstrated here may also be used similarly and have advantages in different formulations. One example is the use of biodegradable gels, i.e. by using a low concentration of gelling ions in order to limit the treatment period. In the treatment of cancer patients a space-filling gel containing drugs or radioactive isotopes may be applied during surgical procedures in order to prevent recidive of the disease. After the active substances are released or radioactivity has decayed it may be desirable that the gel dissolves and is excreted from the body. Self-gelling alginate controlled delivery formulations may of course also be injected directly into the body without any surgical procedures and the gel/alginate solution may also be used for oral drug delivery. For oral use alginate is currently well known in formulations as an anti-reflux remedy. It is therefore also possible that alginate self-gelling formulations may find similar uses.

Example 9

Tissue Engineering Applications

The entrapment of cells within the alginate gel as presented here may be used to produce implantable "biofactories"

excreting active substances for the treatment of a variety of diseases. However, the entrapment of cells within the alginate gel may also be used in tissue engineering applications. For tissue engineering the growth of cells within or on 3-dimensional constructs is needed and therefore good biomaterials for such applications are needed. The time-delayed release of cross-linking ions allow the gelling-ion alginate suspension to be molded into complex geometries before gelation occurs. Under ex vivo conditions such alginate structures may be used as a growth substrate in the development of tissue or artificial organs. Cells grow on the surface of alginate gel beads as the gel surface may be a growth substrate for cells. The growth of cells on alginate gels have been found to be dependent of the alginate and the gelling ions used. The present self-gelling formulation may be used to create multiple layers of cells growing inside or on the surface of alginate sheets or other shaped gel structures. Furthermore, the alginate gel may later be removed through treatment with citrate, phosphates or other gelling ion chelating agents. This gives the possibility to combine several cell layers in the construction of tissues or organs. Several types of cells inside or on the surface of gel structures may be combined if this is desirable for the development of the construct.

Nerve regeneration is an interesting example of the use of alginate within tissue engineering. The filling of artificial nerve conduits with self-gelling alginate may be suitable for the creation of constructs with improved guidance and biocompatibility for nerve regrowth. This system may give better flexibility and better control over molding processes and structure properties as compared to other techniques.

Injectable alginate/cell suspension systems may also be delivered to the defective or damaged tissue site even without surgical intervention. For such applications it may be critical to have a certain working time to shape the material before it gels. However, the gelation rate may also be required to be reasonable rapid so that a prolonged patient waiting time or problems with applying the gel/solution can be avoided. The self-gelling system may as shown here and previously mentioned be adapted with different gelling time-curves and different strength and stability properties. This variability may therefore be used to adapt to each type of injection procedures. As an example the repair of cartilage defects holds a potential for the use self-gelling alginate structures. Alginate has been found to be a useful biomaterial to be used for cartilage tissue engineering, and it has been found that alginate may stimulate chondrogenesis. Therefore self-gelling alginate solutions with or without chondrocytes or other cells may be directly injected in the treatment of articular defects. Osteoarthritis patients are already today being treated with "joint fluid therapy" and there are two products on the market, sodium hyaluronate (Hyalgan) and hylan G-F 20 (Synvisc) which are believed to work as lubricants by supplementing hyaluronic acid, the substance that gives joint fluid its viscosity. Pain relief lasts as long as six to 13 months in some people. The therapies have proven most effective for people with mild to moderate knee osteoarthritis. However, as hyaluronic acid is known to be degraded in the body the use of other biopolymers like alginate with less biodegradability and good biocompatibility provide advantages.

Alginate hydrogels may be lyophilized or the water be removed partly or fully in other ways treated in order to create biocompatible structures like sponges or fibers. The use of the technology presented here, using self-gelling alginate systems, may also be used as a step in the manufacturing of biocompatible sponges or other structures which are useful for tissue engineering or other applications.

Self gelling alginate formulations may be used in the coating of stents or grafts or other implantation devices. Depending of the type of alginate formulation the coating layer may be made more or less biodegradable and give more or less support for the ingrowth of host cells or the growth of cells added to the device.

Example 10

Tissue Bulking

Alginate may be delivered into the submucosa proximal to the urethral sphincter to provide bulking for the treatment of bladder incontinence and procedures has already been performed in the clinic. Another example may be the delivery of alginate formulations at the junction between the esophagus and the stomach to aid in the treatment of gastro-esophageal reflux disorders. The high degree of compatibility of alginates makes the use as an injectable solution in cosmetic procedures an attractive alternative to other materials.

Formulations based upon self-gelling alginate systems may be used to create injectable solutions or pastes with predefined hardening time with purpose of filling a predefined volume. As previously mentioned gel formulations may be made more or less biodegradable giving the bulking formulation a desirable property.

Example 11

Embolization of Blood Vessels

Methods for forming endovascular occlusions may be used to treat conditions such as arteriovenous malformations, aneurysms, excessive blood supplied to tumors, control of massive vascular hemorrhaging, and other conditions which require an embolization to alleviate the condition. Some embolic systems include the use of polymers solutions which begin to solidify or precipitate when contacted with blood or other bodily fluids. Such systems, however, suffer from the problem of the polymer solution migrating into undesired parts of the body because of the time delay necessary to cause formation or precipitation of the solid polymer. Migration in these polymer solution systems is particularly problematic when the solution is injected into "high flow" areas, such as vascular systems. Fibers formed from polymer solution systems also tend to suffer from other problems, such as not embolizing well, being overly brittle, or not being biocompatible. The use of particles or beads of PVA (Poly vinyl alcohol) or gelatin beads have been found useful for embolization and are currently used in clinics.

Alginate based formulations have also been proposed for use in embolization procedures. It has been suggested that endovascular occlusions may be induced using calcium alginate by controlling the injections of an alginate liquid and a calcium chloride solution to meet and polymerize at a site within the vascular system targeted for occlusion. Compared to such systems, the use of self-gelling alginate formulations as presented here have advantages. Treatment may be performed as single injections and the strength of the self-hardening formulation may be adjusted with better control of the system. In particular self-gelling alginate formulations are useful when the time before gelling and biodegradability needs to be controlled.

Example 12

Anti-Adhesion Formulations

Formation of adhesions are attributable to surgical operations, trauma, infections etc. Adhesions frequently occur after abdominal operations and represent a major clinical problem resulting in intestinal obstruction, infertility, and pain. Efforts to prevent or reduce adhesions have largely been unsuccessful; however, recently developed mechanical barriers using different biopolymers have demonstrated clinical progress in adhesion prevention.

Alginate based formulations have also been proposed as anti adhesion barriers. Anti-adhesion barriers may be formulated by using the self-gelling alginate system presented here. The solution/gel formulation is premixed immediately before use and made with suitable biodegradability. Such types of formulations may also include other polymers, drugs or other supportive compounds. Additional polymers may be used to improve the properties of the gel, among others to increase the adhesion between gel structure and tissue.

Example 13

Wound Healing Formulations

Alginate dressings are commonly used to treat exuding wounds. Current alginate products for wound healing are composed of soft, non-woven fibers or pads. Alginates can absorb many times their own weight and form a gel within the wound to fill in dead space and maintain a moist environment. It has also been suggested that alginates may influence the wound healing process through more unknown mechanisms, and it has been postulated that calcium present within alginate wound dressing may influence the would healing process through influence on certain cells.

Self-gelling alginate structures are capable of conforming to the three dimensional structure of a tissue surface during healing processes. Among other formulations with a more controllable and defined calcium content may be achievable as well as structures with high degree of resorbability.

Example 14

Insoluble Calcium Alginate Production

A calcium alginate was prepared using an ultrapure (reduced endotoxin content) commercial alginate. In addition, the calcium content was of a stoichiometric nature. Specifically 60 g of PRONOVA UP LVG sodium alginate (batch FP-008-04) having a molecular weight of approximately 130,000, a viscosity of approximately 150 mPas (1% solution, 20° C.), a guluronate content of 64%, and an endotoxin content of 260 EU/gram, was dissolved in 5 liters of purified water. 26 grams of sodium carbonate was added. 165 grams of calcium chloride dehydrate was first dissolved in 500 ml of purified water and the pH was adjusted with nitric acid to neutrality. The alginate solution was added carefully to the calcium chloride solution under continuous stirring. The precipitated calcium alginate was then washed successively 4 to 8 times with purified water until the conductivity was reduced to a level similar to that of purified water. The washed calcium alginate was then dried under vacuum and subsequently milled. Insoluble strontium alginate may be prepared by similar a method using strontium salt in place of calcium chloride. Resulting insoluble alginates have controlled stoichiometric or sub stoichiometric amounts of calcium or strontium which when used in the gelling systems produce gels of reproducible consistency greater than those made using insoluble alginates produced by other methods.

Example 15

Gelling in the Presence of Other Ions and Calcium Binding Agents

Figure 8:
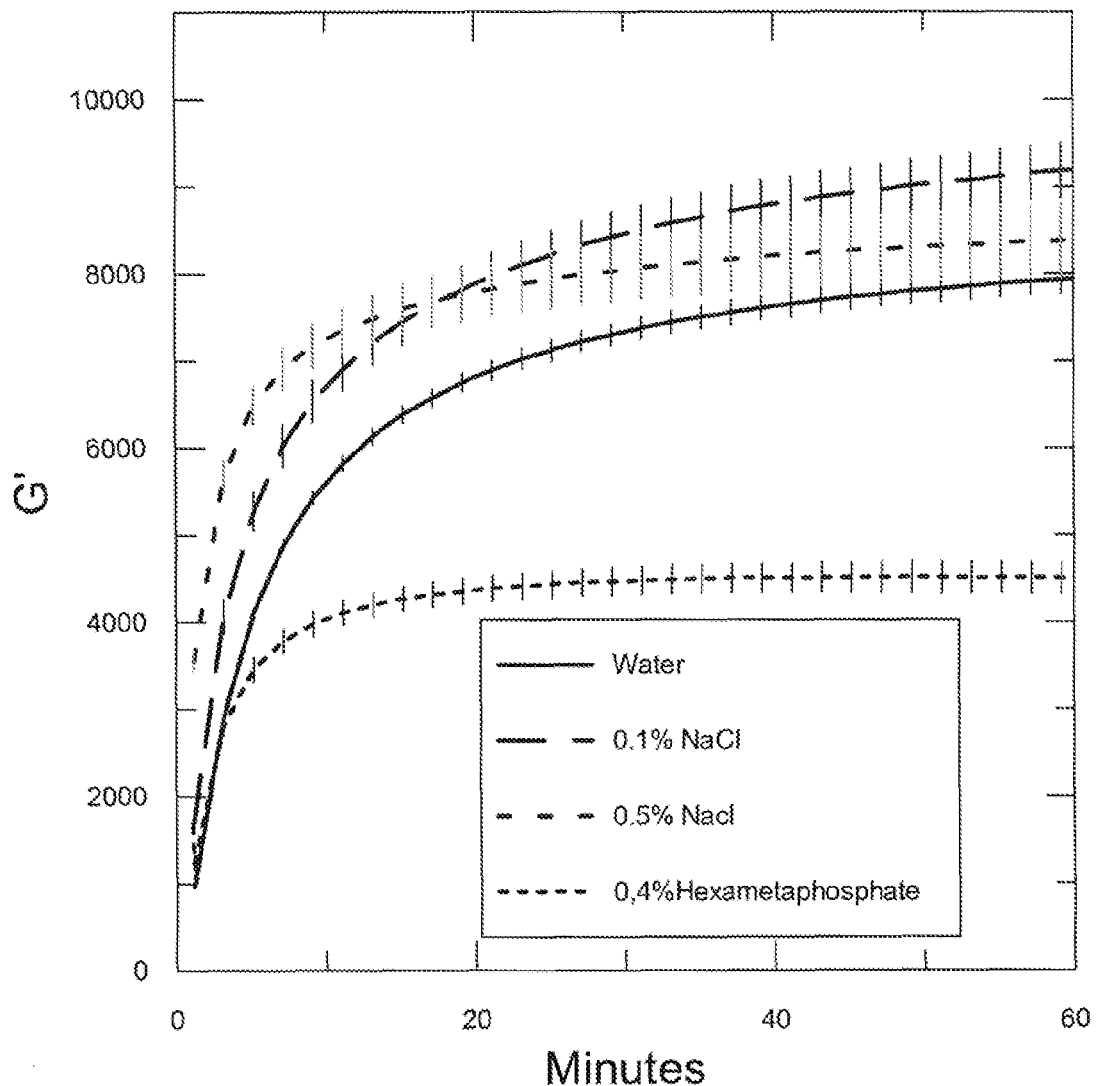
FIG. 8 contains data from rheometer measurements. Oscillation measurements were performed using a Physica MCR300 rheometer. Storage modulus as a function of time for gels containing 1.25% sodium alginate (PRONOVA UP 100 G) mixed with 5.5% strontium alginate (Example 14) at a ratio of 4:1 (final alginate concentration was 2.1%) in the presence or absence of sodium chloride or sodium hexametaphosphate. Each curve is the mean of three independent measurements (curves) with standard error of the mean shown for each point.

In the experiments we performed oscillation measurements as described earlier (Example 1). Storage modulus was measured as a function of time for gels containing 1.25% sodium alginate (PRONOVA UP 100 G) mixed with 5.5% strontium alginate (Example 14) at a ratio of 4:1 (final alginate concentration was 2.1%). The development of the gel was measured in the presence or absence of sodium chloride or sodium hexametaphosphate (FIG. 8). Two different concentrations of sodium chloride was tested and the data clearly demonstrates an increased gelling rate when increasing the concentration of sodium ions. The presence of a calcium binding agent like sodium hexametaphosphate clearly also changed gelling kinetics and reduced the final strength of the gel. The data thus show that the presence of non gelling ions like sodium or calcium complexing compounds like hexametaphosphate may be used to modify gelling kinetics and final properties of the gel.

Example 16

Gelling with Different Sized Calcium Alginate Particles

Figure 9:
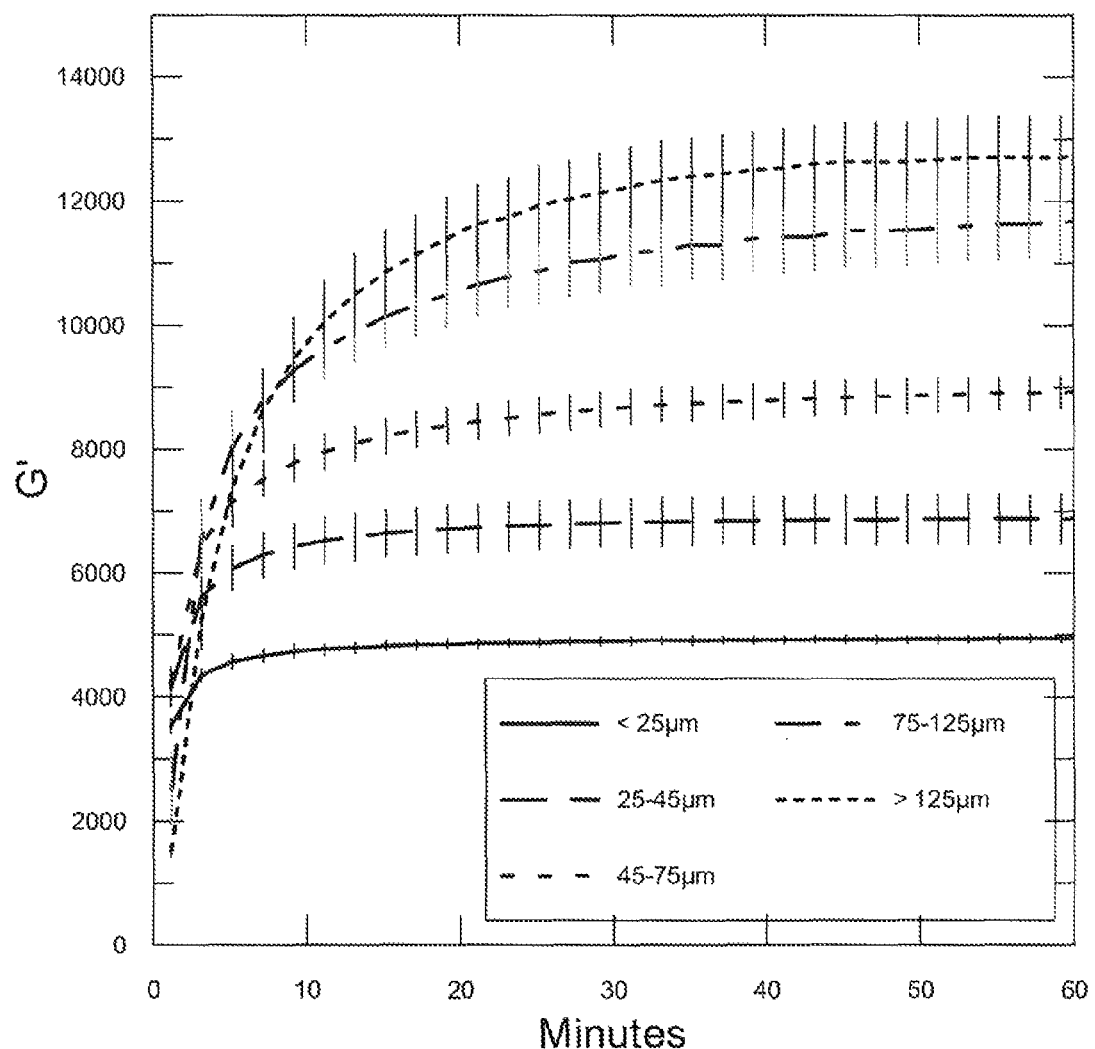
FIG. 9 contains data from rheometer measurements. Oscillation measurements were performed using a Physica MCR300 rheometer. Storage modulus as a function of time for gels containing 1.25% sodium alginate (PRONOVA UP 100 G) mixed with 5.5% calcium alginate (Example 14) manufactured at different particle sizes at a ratio of 4:1 (final total alginate concentration was 2.1%). The different particles sizes were made by milling freeze dried calcium alginate and sifting at the sizes indicated. Each curve is the mean of three independent measurements with standard error of the mean shown for each point.

During the manufacturing process for insoluble alginates the particle size of the final product may be controlled. In this example we made one batch of calcium alginate that was milled and sifted through different filters in order to separate between different particle sizes. When the different strontium alginate particles were gelled with sodium alginate under otherwise identical conditions there was a large difference in the gelling process and final properties of the gel (FIG. 9). While the gelling was very rapid for the smaller particle sizes, the total gelling time was considerably longer for the larger particle sizes and this also gave gels with much higher strength. However, for the smaller particle sizes it should be noted that some degradation of the gel probably occurred during mixing of the two components as the gelling speed was very rapid (in particular for particles less than 25 µm). This effect may therefore also contribute somewhat to the difference in final gel strength. Nevertheless, in conclusion our data shows that the particles size needs to be accounted for and may be actively used in order to obtain desirable properties.

Example 17

Gelling at Different Temperatures

Figure 10:
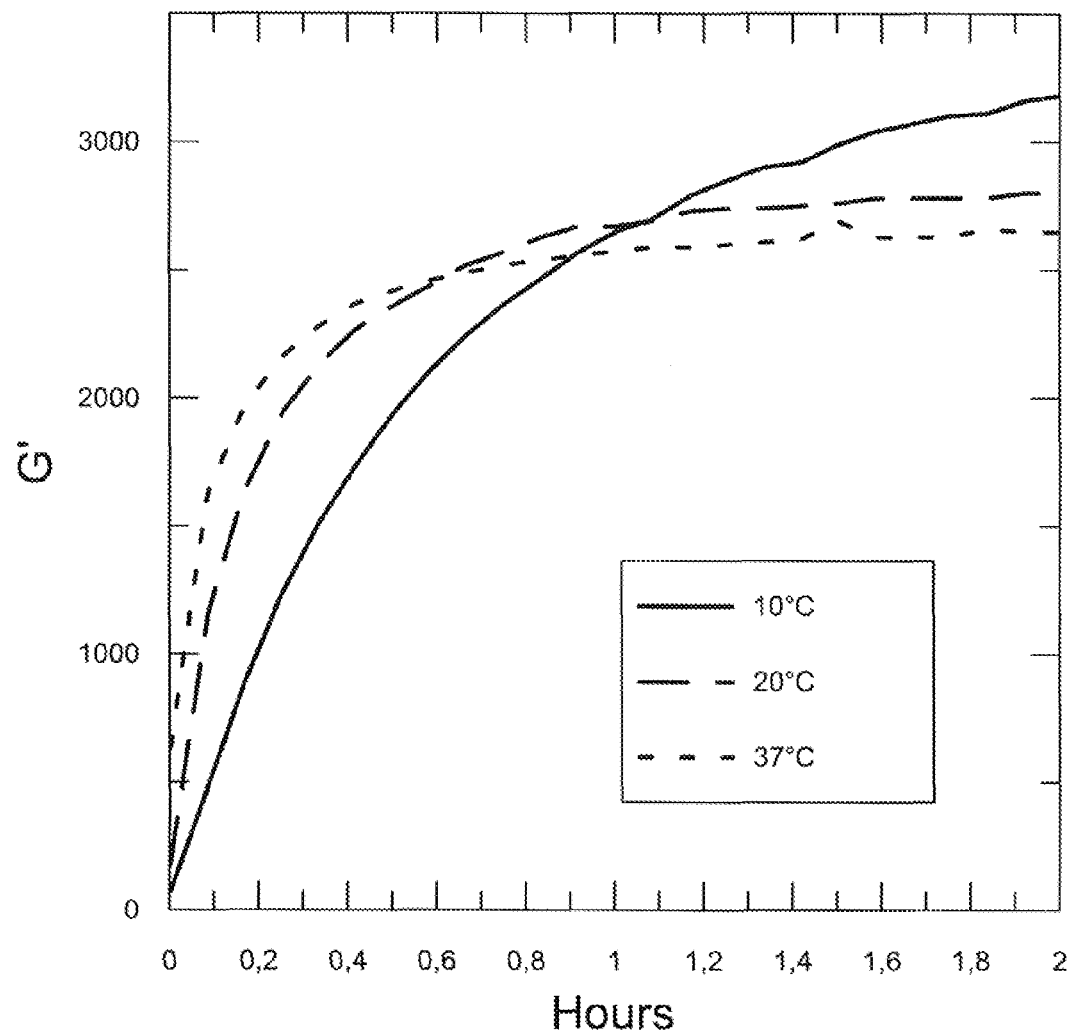
FIG. 10 contains data from rheometer measurements. Oscillation measurements were performed using a Physica MCR300 rheometer. Storage modulus as a function of time for gels containing 1.25% sodium alginate (PRONOVA UP LVG) mixed with 10% calcium alginate (Example 14) at different temperatures at a ratio of 9:1 (final alginate concentration was 2%).

We also tested whether adjusting the temperature could be actively used to control the setting of the gel system. In FIG. 10 is shown rheological data for a mixture of calcium alginate and sodium alginate at different temperatures. Clearly, the gelling rate was reduced at 10° C. and also increased at 37° C. as compared to room temperature. The data thus shows that the temperature may be actively used in order to control gelling kinetics. Among others this could be actively used by reducing the temperature to allow more time for gel preparation and handling before administration in vivo.

Example 18

Gelling with Non-Saturated Calcium or Strontium Alginate Particles

Calcium alginates and strontium alginates were prepared which were stoichiometric non-saturated with gelling ions (less than 100% saturated). Such particles in contrast to the saturated particles rehydrated very rapidly in contact with water containing solutions. The non-saturated particles therefore could be used to form an instant gel structure consisting of gel particles (non solid gel). Although the gel structure was weak it was easily shapeable for a long period. Cells or other materials could easily be mixed into the gel structure by simply adding them to the water containing solution before mixing in the powder. Also other particles or materials could be mixed into the gel structure by premixing with the non-saturated particles before adding the water containing solution. One example of this is to premix dry sodium alginate, saturated insoluble alginate and non-saturated insoluble alginate before the water containing solution is added. In contact with water this mixture as previously will give an instant water absorbing gel structure, however, the gel strength will also increase further with time as the particles of soluble alginate and insoluble saturated alginate in the gel gradually starts to hydrate and gel upon dissolving. The formulations mentioned here, utilizing the water absorbing properties of non-saturated insoluble alginates may thus also be used in combinations with cells or other materials and be very useful for tissue engineering and other applications.

Example 19

FP-411-03, Production of Calcium Alginate with Stoichiometric Amount of Calcium (100% Saturation), G-Rich Alginate, with Sodium Carbonate and Nitric Acid 50 grams of PRONOVA UP LVG sodium alginate, batch FP-008-04 (64% guluronic acid content, 130,000 g/mol molecular weight, 146 mPas viscosity of a 1% solution at 20° C., 400 EU/gram endotoxin content) were dissolved in 3 liters of purified water. 15 grams of sodium carbonate was added. A calcium solution was added consisting of 139 grams of $CaCl_2.2H_2O$ dissolved in 300 ml of purified water with the addition of 12 ml $HNO_3$ (65%). A fine precipitation resulted. The conductivity of this solution was measured to be 55 mS/cm. The precipitate was washed successively (8 times) with purified water until the conductivity was 0.08 mS/cm. The precipitate was vacuum dried.

Example 20

FP-411-04, Production of Calcium Alginate with Sub-Stoichiometric Amount of Calcium (50% Saturation), G-Rich Alginate, with Sodium Carbonate and Nitric Acid 25 grams of PRONOVA UP LVG (description as given in Example 19) was dissolved in 1.5 liters of purified water. To calculate the amount of calcium required, 25 grams of alginate represent 0.146 mol of alginate (using a monomer molecular weight of 171 g/mol). The alginate used, PRONOVA UP LVG batch FP-008-04 has a guluronic acid content of 64% which results in 0.093 mol of calcium-binding sites (0.146 mol of alginate×64% guluronic acid monomers). For a 50% substitution with calcium this would require 0.0465 mol of calcium (0.093/2=0.0465 mol). 0.0465 mol of calcium salt is calculated to be 6.84 grams of the dihydrate (0.0465 mol×147.02 g/mol ($CaCl_2.2H_2O$)=6.84 g of $CaCl_2.2H_2O$. 6.84 grams of $CaCl_2.2H_2O$ are dissolved in 150 ml purified water and 6 ml of $HNO_3$ (65%). 7.5 grams of sodium carbonate are added to the alginate solution. A fine precipitation results. The conductivity is measured to be 8 mS/cm. The precipitate is washed successively (6 times) until the conductivity is 0.4 mS/cm. The precipitate is vacuum dried.

Example 21

FP-411-05, Production of Strontium Alginate with Stoichiometric Amount of Strontium (100% Saturation), G-Rich Alginate, with Sodium Carbonate and Nitric Acid 47 grams of PRONOVA UP LVG sodium alginate, batch FP-008-04 (64% guluronic acid content, 130,000 g/mol molecular weight, 146 mPas viscosity of a 1% solution at 20° C., 400 EU/gram endotoxin content) were dissolved in 3 liters of purified water. 15 grams of sodium carbonate was added. A strontium solution was added consisting of 252 grams of $SrCl_2.6H_2O$ dissolved in 300 ml of purified water with the addition of 12 ml $HNO_3$ (65%). A fine precipitation resulted. The conductivity of this solution was measured to be 78 mS/cm. The precipitate was washed successively (8 washes) with purified water until the conductivity was 0.0159 mS/cm. The precipitate was vacuum dried.

Example 22

FP-411-06, Production of Strontium Alginate with Sub-Stoichiometric Amount of Strontium (50% Saturation), G-Rich Alginate, with Sodium Carbonate and Nitric Acid 23.3 grams of PRONOVA UP LVG (description as given in Example 19) was dissolved in 1.5 liters of purified water. To calculate the amount of calcium required, 23.3 grams of alginate represent 0.136 mol of alginate (using a monomer molecular weight of 171 g/mol). The alginate used, PRONOVA UP LVG batch FP-008-04 has a guluronic acid content of 64% which results in 0.087 mol of calcium-binding sites (0.136 mol of alginate×64% guluronic acid monomers). For a 50% substitution with strontium this would require 0.0435 mol of strontium (0.087/2=0.0435 mol). 0.0435 mol of strontium salt is calculated to be 11.6 grams of the hexahydrate (0.0435 mol×266.62 g/mol ($SrCl_2.6H_2O$)=11.6 g of $SrCl_2.6H_2O$. 11.6 grams of $SrCl_2.6H_2O$ are dissolved in 150 ml purified water and 6 ml of $HNO_3$ (65%). 7.5 grams of sodium carbonate are added to the alginate solution. A fine precipitation results. The conductivity is measured to be 22 mS/cm. The precipitate is washed successively (3 times) until the conductivity is 0.6 mS/cm. The precipitate is vacuum dried Example 23

FP-506-03, Production of Strontium Alginate with Stoichiometric Amount of Strontium (100% Saturation), M-Rich Alginate, without Sodium Carbonate and Nitric Acid 50 grams of PRONOVA UP LVM sodium alginate, batch FP-408-01 (44% guluronic acid content, 220,000 g/mol molecular weight, 127 mPas viscosity of a 1% solution at 20° C., <25 EU/gram endotoxin content) were dissolved in 3 liters of purified water. A strontium solution was added consisting of 252 grams of $SrCl_2.6H_2O$ dissolved in 400 ml of purified. A fine precipitation resulted. The conductivity of this solution was measured to be 43 mS/cm. The precipitate was washed successively (8 washes) with purified water until the conductivity was 0.143 mS/cm. The precipitate was vacuum dried, milled and fractionated.

Example 24

FP-505-05, Production of Strontium Alginate with Stoichiometric Amount of Strontium (100% Saturation), G-Rich Alginate, without Sodium Carbonate or Nitric Acid

50 grams of PRONOVA UP LVG sodium alginate, batch FP-408-02 (69% guluronic acid content, 219,000 g/mol molecular weight, 138 mPas viscosity of a 1% solution at 20° C., <25 EU/gram endotoxin content) were dissolved in 3 liters of purified water. A strontium solution was added consisting of 252 grams of $SrCl_2.6H_2O$ dissolved in 400 ml of purified. A fine precipitation resulted. The conductivity of this solution was measured to be 40 mS/cm. The precipitate was washed successively (7 washes) with purified water until the conductivity was 0.1 mS/cm. The precipitate was vacuum dried, milled and fractionated.

Example 25

FP-505-02, Production of Calcium Alginate with Stoichiometric Amount of Calcium (100% Saturation), M-Rich Alginate, without Sodium Carbonate and Nitric Acid

50 grams of PRONOVA UP LVM sodium alginate, batch FP-408-01 (44% guluronic acid content, 220,000 g/mol molecular weight, 127 mPas viscosity of a 1% solution at 20° C., <25 EU/gram endotoxin content) were dissolved in 3 liters of purified water. A calcium solution was added consisting of 137 grams of $CaCl_2.2H_2O$ dissolved in 300 ml of purified water. A fine precipitation resulted. The conductivity of this solution was measured to be 45 mS/cm. The precipitate was washed successively (8 washes) with purified water until the conductivity was 0.0129 mS/cm. The precipitate was vacuum dried, milled and fractionated.

Example 26

FP-504-02, Production of Calcium Alginate with Stoichiometric Amount of Calcium (100% Saturation), G-Rich Alginate, without Sodium Carbonate and Nitric Acid

50 grams of PRONOVA UP LVG sodium alginate, batch FP-408-02 (69% guluronic acid content, 219,000 g/mol molecular weight, 138 mPas viscosity of a 1% solution at 20° C., <25 EU/gram endotoxin content) were dissolved in 5 liters of purified water. A calcium solution was added consisting of 231 grams of $CaCl_2.2H_2O$ dissolved in 500 ml of purified. A fine precipitation resulted. The conductivity of this solution was measured to be 43 mS/cm. The precipitate was washed successively (8 washes) with purified water until the conductivity was 0.0068 mS/cm. The precipitate was vacuum dried, milled and fractionated.

Example 27

Further Examples of Products Produced with Varying Stoichiometries of Calcium and Strontium Content, as Well as Variations in the Type of Alginate Used (Guluronate-Rich (G) or Mannuronate-Rich (M)) are Shown in the Attached Table

| Batch | Salt | Alginate type Viscosity, mPas | Saturation | % Na | % Ca | % Sr | Particle size, μm |
|---|---|---|---|---|---|---|---|
| FP-508-03 | Ca | G 113 | 100% | | | | 125, 75, 45, 25 |
| FP-506-03 | Sr | M 127 | 100% | | | | 125, 75, 45, 25 |
| FP-505-05 | Sr | G 425 | 100% | | | | 125, 75, 45, 25 |
| FP-505-02 | Ca | M 410 | 100% | | | | 125, 75, 45, 25 |
| FP-504-02 | Ca | G 993 | 100% | | | | |
| FP-502-02 | Sr | M 663 | 100% | 0.12 | | 21.6 | 75 |
| FP-502-01 | Ca | M 663 | 100% | 0.16 | 9.2 | | 75 |
| FP-501-06 | Sr | G 149 | 100% | 0.58 | | 20.5 | |
| FP-501-05 | Ca | G 149 | 100% | 0.44 | 8.0 | | |
| FP-501-03 | Sr | M 110 | 100% | | | | |
| FP-501-02 | Ca | M 110 | 100% | 0.22 | 8.6 | | |
| FP-412-01 | Sr | M 110 | 90% | 3.1 | | 14.5 | |
| FP-411-06 | Sr | G 146 | 64% | | | | |
| FP-411-05 | Sr | G 146 | 100% | 0.46 | | 20.0 | |
| FP-411-04 | Ca | G 146 | 64% | 3.4 | 6.4 | | |
| FP-411-03 | Ca | G 146 | 100% | 0.16 | 9.5 | | |
| 16.09.2004 | Ca | G 190 | 100% | 0.21 | 10.3 | | |

The invention claimed is:

1. A method of using an alginate gel as a tissue bulking material in an individual comprising dispensing a self gelling alginate dispersion within an individual; wherein said self gelling alginate dispersion is dispensed within an individual in a process comprising:
   a) forming a dispersion by mixing i) a solution comprising a soluble alginate with an insoluble alginate/gelling ion particles or ii) immediately soluble alginate, insoluble alginate/gelling ion particles and a solvent, and
   b) dispensing the dispersion in an individual whereby the dispersion forms an alginate gel matrix.

2. The method of claim 1 wherein the alginate gel is used as tissue bulking material for treatment of bladder incontinence, wherein said self gelling alginate dispersion is dispensed into the submucosa proximal to the urethral sphincter of the individual or the alginate gel is used as tissue bulking material for treatment of gastro-esophageal reflux disorders, wherein said self gelling alginate dispersion is dispensed at the junction between the esophagus and stomach of an individual.

* * * * *